United States Patent
David

(10) Patent No.: US 10,254,201 B2
(45) Date of Patent: Apr. 9, 2019

(54) AUTOMATIC AIR-SAMPLING AND PNEUMATIC TRANSPORT SYSTEM WITH BALL-FILTER HOPPER AND INTEGRATED SAMPLING MANIFOLD

(71) Applicant: Brian J. David, Falls Church, VA (US)

(72) Inventor: Brian J. David, Falls Church, VA (US)

( * ) Notice: Subject to any disclaimer, the term of this patent is extended or adjusted under 35 U.S.C. 154(b) by 250 days.

(21) Appl. No.: 15/368,198

(22) Filed: Dec. 2, 2016

(65) Prior Publication Data
US 2017/0328815 A1 Nov. 16, 2017

Related U.S. Application Data

(63) Continuation-in-part of application No. 15/098,405, filed on Apr. 14, 2016, now Pat. No. 10,041,864.
(Continued)

(51) Int. Cl.
| | |
|---|---|
| *B01D 46/00* | (2006.01) |
| *B01D 46/42* | (2006.01) |
| *G01N 1/22* | (2006.01) |
| *G01N 1/24* | (2006.01) |
| *G01N 1/40* | (2006.01) |

(Continued)

(52) U.S. Cl.
CPC ....... *G01N 1/2273* (2013.01); *B01D 46/0036* (2013.01); *B01D 46/42* (2013.01); *G01N 1/2205* (2013.01); *G01N 1/24* (2013.01); *G01N 1/405* (2013.01); *G01N 1/4077* (2013.01); *G01N 33/0036* (2013.01); *G01N 33/0055* (2013.01); *B01D 2273/14* (2013.01);
(Continued)

(58) Field of Classification Search
CPC .................................................. B01D 46/0036

USPC ...................................................... 73/863.23
See application file for complete search history.

(56) References Cited

U.S. PATENT DOCUMENTS

| 4,381,681 A | 5/1983 | Bell |
| 4,391,151 A | 7/1983 | Nelson et al. |

(Continued)

OTHER PUBLICATIONS

Asbestos Sampling, Nov. 17, 1994, Environmental Protection Agency.
(Continued)

*Primary Examiner* — Justin Seo
*Assistant Examiner* — Jean F Morello
(74) *Attorney, Agent, or Firm* — Clyde E. Findley

(57) ABSTRACT

Embodiments of the invention can sample particulates, aerosols, vapors, and/or biological components of ambient air utilizing spherical air-sampling filters. Components of the embodiments may include a hopper for holding spherical air-sampling filters, an air-sampling manifold configured to deliver an air-sampling filter from the hopper to a sampling location, and an air compressor to perform an air sampling operation and to transport a used air-sampling filter away from the sampling location. Operation of some embodiments may begin by rotating a slotted drum within the air-sampling manifold to deliver an air-sampling filter from the hopper to the sampling position. Operation may continue by using the air compressor to draw air from an ambient environment through the air-sampling filter. After sampling is complete, the air compressor may be utilized to pneumatically transport the used air-sampling filter away from the sampling position to a filter retrieval location via an output tube.

6 Claims, 16 Drawing Sheets

Related U.S. Application Data which is a continuation of application No. 14/466,132, filed on Aug. 22, 2014, now Pat. No. 9,341,547, application No. 15/368,198, which is a continuation-in-part of application No. 15/297,785, filed on Oct. 19, 2016, which is a continuation of application No. 14/466,132.

(60) Provisional application No. 61/959,659, filed on Aug. 29, 2013.

(51) Int. Cl.
*G01N 33/00* (2006.01)
*G01N 1/18* (2006.01)
*G01N 35/04* (2006.01)

(52) U.S. Cl.
CPC ............... *G01N 2001/185* (2013.01); *G01N 2001/2223* (2013.01); *G01N 2001/4088* (2013.01); *G01N 2033/0093* (2013.01); *G01N 2035/0481* (2013.01); *Y02A 50/25* (2018.01)

(56) References Cited

U.S. PATENT DOCUMENTS

| | | |
|---|---|---|
| 4,570,494 A | 2/1986 | Dunn et al. |
| 4,869,117 A * | 9/1989 | McAndless .......... G01N 1/2214 73/864.34 |
| 5,404,762 A | 4/1995 | Rodgers et al. |
| 5,691,487 A | 11/1997 | Green et al. |
| 6,023,982 A * | 2/2000 | Basch .................. G01N 1/2273 73/863.25 |
| 6,096,267 A | 8/2000 | Kishkovich et al. |
| 6,477,906 B1 | 11/2002 | Peterson |
| 6,854,344 B2 | 2/2005 | Cornish et al. |
| 8,196,479 B2 | 6/2012 | Ludwick et al. |
| 8,254,696 B2 | 8/2012 | Matteoni et al. |
| 8,978,491 B2 | 3/2015 | Sinclair et al. |
| 2008/0304752 A1 | 12/2008 | Matteoni et al. |
| 2009/0131818 A1 | 5/2009 | Speeg et al. |
| 2014/0249451 A1 | 9/2014 | Mao et al. |
| 2016/0054204 A1 | 2/2016 | David |

OTHER PUBLICATIONS

Benjamin Brodsky, The Next Generation of Sensor Technology for the BioWatch Program, Sep. 1, 2007, NTI.
Alexander Garza, The Truth About BioWatch: The Importance of Early Detection of a Potential Biological Attack, Jul. 12, 2012, DHS.
Michael V. Walter, BioWatch Overview, Jun. 25, 2013, DHS.
Porex Life Science Products, Media & Filters, 2014, www.porex.com.

* cited by examiner

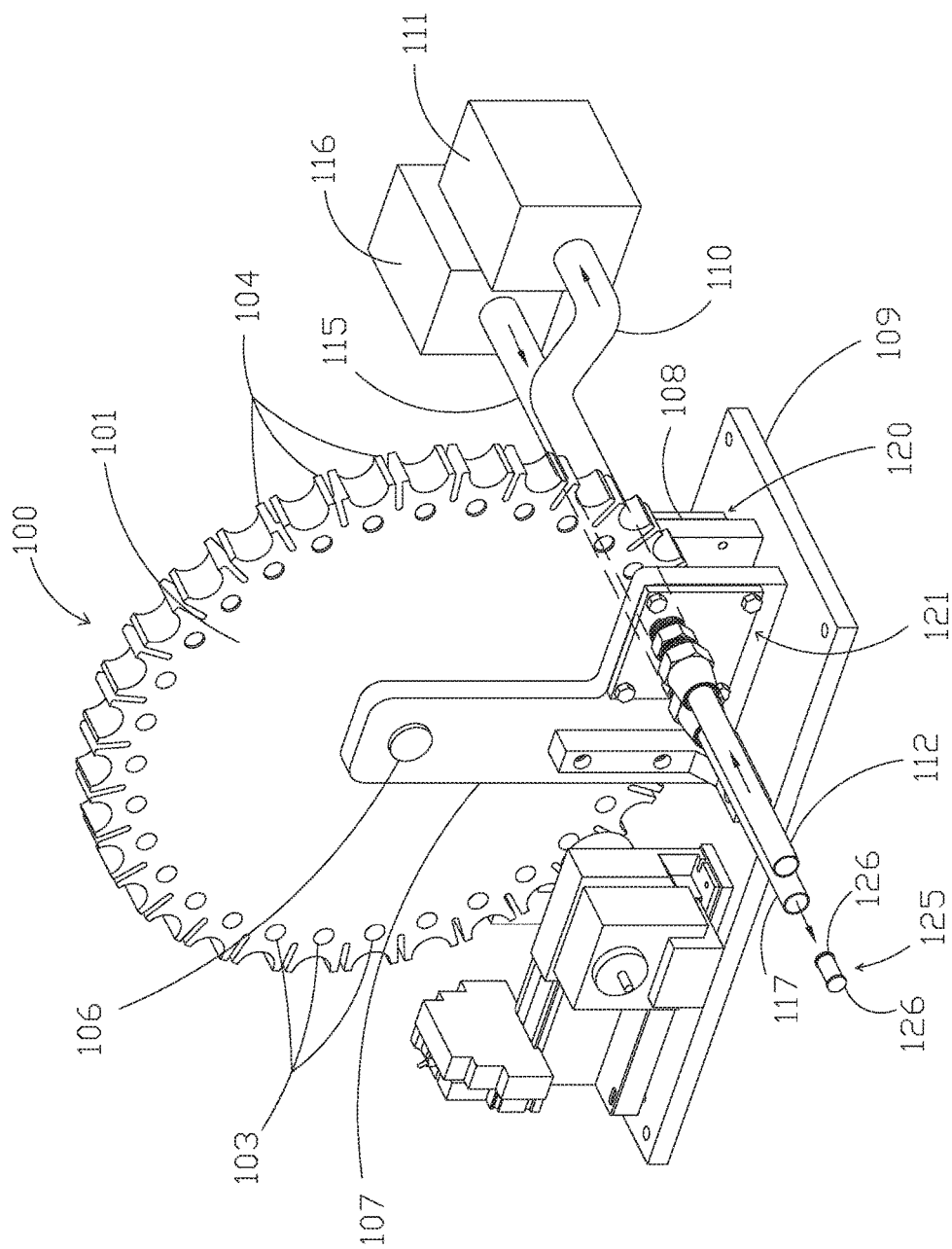

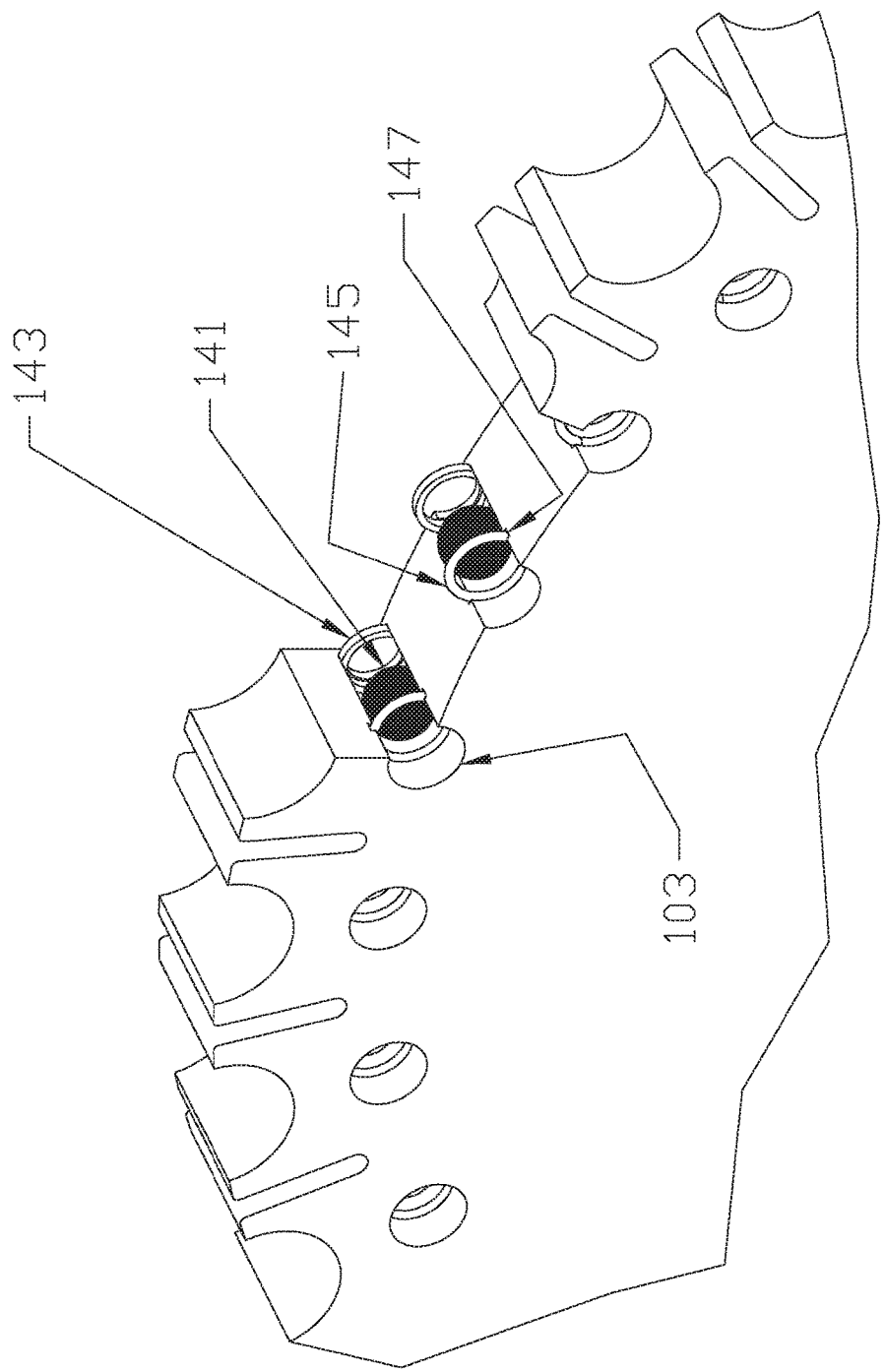

AUTOMATIC AIR-SAMPLING AND PNEUMATIC TRANSPORT SYSTEM WITH BALL-FILTER HOPPER AND INTEGRATED SAMPLING MANIFOLD

CROSS REFERENCE TO RELATED APPLICATIONS

This application is a continuation-in-part of U.S. patent application Ser. No. 15/098,405, filed on Apr. 14, 2016, which is a continuation of U.S. patent application Ser. No. 14/466,132, now U.S. Pat. No. 9,341,547, filed on Aug. 22, 2014, which claims priority under 35 U.S.C. § 119(e) to U.S. Provisional Patent Application No. 61/959,659, filed on Aug. 29, 2013. This application is also a continuation-in-part of U.S. patent application Ser. No. 15/297,785, filed on Oct. 19, 2016, which is a continuation of U.S. patent application Ser. No. 14/466,132. All of these applications are hereby incorporated by reference.

BACKGROUND

The present invention is related to the field of air sampling. More particularly, the present invention is related to systems that automatically collect samples of air and optionally transport those samples away from a sampling site. Still more particularly, the present invention is related to methods, systems, and devices that use a storage magazine with a rotatable slotted drum to supply spherical or ball-shaped porous air-sampling filters to an air-sampling system that can use the spherical air-sampling filters to automatically collect air samples and transport the samples to a retrieval location.

DESCRIPTION OF RELATED ART

Systems that sample air for aerosols, including suspensions of solid or liquid particles, have been used in a wide range of applications. For example, systems have been used to sample and analyze vehicle exhaust to ensure conformance with state pollution regulations. Systems have also been used to analyze the air surrounding suspected targets of biological warfare in order to identify hazardous airborne microorganisms, such as anthrax, and to determine appropriate medical responses. For example, the Environmental Protection Agency routinely samples air around the United States, not only to monitor atmospheric levels of ozone and carbon monoxide, but also to collect representative samples of airborne biological and radiological contaminants. Since aerosols typically diffuse in the air, it is often necessary to first concentrate the aerosols before the samples can be analyzed.

In order to concentrate aerosols, many air-sampling devices pull air through or over a filter, or other sampling medium, over a period of time. While some sampling media can selectively concentrate specific aerosols, other sampling media can concentrate many aerosols collectively, to be separated and analyzed later. Some air-sampling devices can analyze collected samples autonomously, while others require the samples to be retrieved for off-site analysis at a laboratory. The utility of air-sampling devices that can analyze samples autonomously is often constrained by costly and delicate instrumentation needed for specialized analysis of the air samples. For example, coupling a Polymerase Chain Reaction ("PCR") device to an air-sampling device would allow many aerosols to be identified at the DNA level, but would require a significant investment. Automated PCR/Aerosol Sampling machines cost up to several hundred thousand dollars, are difficult and costly to maintain properly, and may not be cost effective given the high maintenance cost in the field. A known example of such a system is the microfluidic bio-agent autonomous networked detector ("M-BAND") produced by PositiveID Corporation, which was one of two candidates in development for use in the Department of Homeland Security's ("DHS") BioWatch Gen 3 program. The DHS program subsequently was canceled due to high costs, false positive results, and frequently required maintenance. A more practical and more cost-effective approach separates sample collection from analysis, but requires air samples to be manually retrieved from the sampling site and transported off-site to a laboratory. This is the current ongoing DHS BioWatch Gen 2 program.

All known air-sampling devices that collect and store air samples require an operator to retrieve air samples from the device at the sampling site. For example, the Portable Multi-Tube Air Sampler Unit disclosed in U.S. Pat. No. 8,196,479 encases multiple air sample-collection tubes into a portable container and requires an operator not only to deliver and activate the device at the sampling site, but also later to return in order to retrieve the entire unit, including the air samples contained within.

The Automatic Multi-Sorbent Tube Air Sampler ("AM-TAS") disclosed in U.S. Pat. No. 6,477,906 can be installed at a sampling site to collect air samples autonomously at a later time, but it also requires an operator to retrieve the air samples whenever analysis is needed. Although the AMTAS is capable of allowing individual air samples to be removed during continued operation, the Portable Multi-Tube Air Sampler Unit and most other air-sampling devices require an operator to wait until the end of operation before the collected air samples can be retrieved.

Despite the benefits provided by the prior art systems, they nevertheless fall short of providing a system that eliminates the necessity for an operator to be present at the sampling site, either for the loading of individual air-sampling cartridges, the retrieval of individual used air-sampling cartridges at the end of operation, or for the retrieval of individual used air-sampling cartridges during continued operation. Instead, prior art systems require a human operator to enter the sampling site wearing appropriate personal protective equipment and to risk contamination to install the device, activate collection, and retrieve air samples. Additionally, prior art systems fall short of providing a system where used air-sampling cartridges can be rapidly retrieved from an air-sampling system while the system continues to operate uninterrupted. Prior art systems rely on a human operator to retrieve samples at the end of an operation or to interrupt an operation to retrieve air-sampling cartridges prior to the end of operation.

SUMMARY

This Summary is provided to introduce certain concepts in a simplified form that are further described below in the Detailed Description. The Summary is not intended to identify key features or essential features of the claimed subject matter, nor is it intended in any way to limit the scope of the claimed invention.

Some embodiments of the invention can sample aerosols by utilizing a vacuum pump to pull ambient air through an air inlet tube and an air-sampling cartridge aligned with the inlet tube, and then transport a used air-sampling cartridge through an aligned outlet tube to a cartridge retrieval location using pneumatic pressure supplied by a compressor. The vacuum pump and the compressor may be the same device.

Some embodiments of the invention can utilize air-sampling cartridges comprising one or more sampling media to collect and concentrate a number of different aerosols and/or vapors. For example, an air-sampling cartridge containing fibrous, membranous, and/or perforated or porous solid filter media can concentrate and collect solid airborne particulates, whereas an air-sampling cartridge containing an adsorbent, such as activated charcoal, can concentrate and collect vapors. Embodiments of the invention can also utilize an air-sampling cartridge comprising a combination of two or more sampling media to collect combinations of aerosols and vapors simultaneously.

In some embodiments, an air-sampling cartridge may comprise an air-sampling filter. For purposes of these embodiments, an air-sampling filter (or simply a filter) is a type of air-sampling cartridge that is made entirely of sampling media, with no separate covering, wrapper, or containing material. In the context of these embodiments, wherever an air-sampling cartridge is utilized, an appropriately configured air-sampling filter may be used instead.

Some embodiments of the invention may have a "sampling position," where an air-sampling cartridge retained in a chamber can collect aerosols and/or vapors from ambient air during a "sampling operation." Additionally, some embodiments of the invention may have a "transport position," where a used air-sampling cartridge can be subjected to pneumatic pressure during a "transporting operation" to be transported away from the transport position in a transport tube. In some embodiments, the sampling position may occupy the same location as the transport position. In other embodiments, there may be a plurality of sampling positions and/or transport positions. In still other embodiments, some or all of the sampling positions may occupy the same location as some or all of the transport positions.

Some embodiments of the invention can arrange a plurality of chambers for retaining air-sampling cartridges in a circular pattern in a wheel assembly and can utilize a rotation mechanism, such as a Geneva drive, to rotate the wheel assembly and change the positions of the plurality of chambers. In such embodiments, the rotation mechanism can also hold the wheel assembly in a stationary position while an air sample is taken in an unused air-sampling cartridge at the sampling position (i.e., during a sampling operation) while, at the same time, a used air-sampling cartridge at the transport position is subjected to pneumatic pressure and transported to a cartridge retrieval location (i.e., during a transport operation).

Alternatively, some embodiments of the invention can arrange a plurality of chambers in a linear arrangement in a rectangular assembly and can utilize a translation mechanism, such as a piston or solenoid, to change the positions of the plurality of chambers. In such embodiments, the translation mechanism can also hold the rectangular assembly in position while an air sample is taken in an unused air-sampling cartridge at the sampling position and while a used air-sampling cartridge at the transport position is subjected to pneumatic pressure and transported to a cartridge retrieval location.

Some embodiments of the invention can move an air-sampling cartridge, such as a spherical air-sampling cartridge, from a storage magazine (i.e., hopper) to a sampling position, and then subsequently to a transport position. The storage compartment and sampling position can be separated by a first gate, or other dividing mechanism, to create a substantially airtight seal between the storage compartment and the air-sampling cartridge in the sampling position. The sampling position and transport position may be separated from each other by a second gate, or other dividing mechanism, to create a substantially airtight seal around the air-sampling cartridge in the transport position.

In some embodiments, the sampling position may occupy substantially the same location as the transport position within an integrated air sampling and transport manifold. In such embodiments, a one-way check valve in an air-sampling tube and/or a one-way check valve in an outlet tube may work separately or together to ensure that air moving through the sampling-transport position is flowing in the proper direction, either to pull ambient air to an unused air-sampling cartridge during a sampling operation or to push a used air-sampling cartridge away from the sampling-transport position and into the outlet tube toward a cartridge retrieval location during a transport operation.

Some embodiments of the invention can permit manual loading of air-sampling cartridges into a plurality of chambers prior to operation, for example by using a hand-held push tool. Other embodiments of the invention can utilize a storage magazine or hopper containing unused air-sampling cartridges, from which an unused air-sampling cartridge can be loaded into an empty chamber by automated mechanical means known to those of ordinary skill in the art. For example, some embodiments of the invention can utilize a combination of a ball hopper and a filter manifold containing a rotatable slotted drum in order to deliver spherical air-sampling cartridges, one at a time, to a sample pipe located in front of a wheel assembly, and then utilize a vacuum pump to pull a spherical air-sampling cartridge from inside the sample pipe into an empty chamber in a wheel assembly.

Some embodiments of the invention can autonomously align a first one of a plurality of chambers retaining an air-sampling cartridge with a sampling position while simultaneously aligning a second one of the plurality of chambers with a transport position. Such autonomous aligning can be triggered by a pre-programmed set of instructions or on demand via remote communication. The remote communication can be facilitated through wired or wireless communication at any distance from the device, such as through a communications device directly interfaced with the system, or through a communications device connected to a local area network or intranet, or on a communications device anywhere in the world connected to the Internet or similar network.

Some embodiments of the invention can form a substantially airtight inlet seal among a vacuum pump, an inlet tube, and a chamber at the sampling position by using a first pair of spring-loaded, double-lipped cups biased against opposite faces of a wheel assembly. Similarly, some embodiments of the invention can form a substantially airtight outlet seal among a compressor, an outlet tube, and a chamber at the transport position by using a second pair of spring-loaded, double-lipped cups biased against opposite faces of a wheel assembly.

Some embodiments of the invention can utilize a vacuum pump to pull ambient air through an air-sampling cartridge retained in a chamber at a sampling position, and can utilize a compressor to apply pneumatic pressure to an air-sampling cartridge retained in a chamber at a transport position, thereby transporting the air-sampling cartridge through tubes to a cartridge retrieval location, which can be nearby or up to several miles away. Such embodiments can utilize both a vacuum pump and a compressor simultaneously to allow simultaneous sampling operation and transport operation.

Some embodiments of the invention can perform the sampling operation and the transport operation using a single compressor. A three-way ball valve, or another similar valve, can be utilized to alternately switch air pathways to connect the compressor with the sampling position or the transport position, to allow a single compressor to perform both vacuum and pressurizing functions.

Some embodiments of the invention can incorporate radiological, chemical, and/or biological detectors to analyze samples within the air-sampling cartridges before they are transported to a cartridge retrieval location, either at a nearby location or at a remote destination. Before transport, an air-sampling cartridge can be aligned with a detector at an analysis position where an air sample can be analyzed within the air-sampling cartridge while still loaded in a chamber.

Some embodiments of the invention can add a pressure transducer connected to a compressor line to measure air pressure in the compressor line and connected components, such as an aligned chamber at a transport position and an outlet tube. Some embodiments of the invention can also use a pressure transducer connected to a vacuum line, to measure air pressure in the vacuum line and connected components, such as the aligned chamber at a sampling position and an inlet tube. In such embodiments of the invention, the pressure transducer can be in communication with a controller or communications board and can relay air pressure data to a remote site.

BRIEF DESCRIPTION OF THE DRAWINGS

So that the manner in which the above recited summary features of the present invention can be understood in detail, a more particular description of the invention may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1A is a perspective view of one embodiment of an automatic re-loading air-sampling and pneumatic transport system constructed in accordance with the teachings of the present invention with a view of a front face of a wheel assembly.

FIG. 1D is a partial perspective view of the same embodiment depicted in FIG. 1A, illustrating a different embodiment that uses a spherical air-sampling cartridge (or filter) rather than a cylindrical air-sampling cartridge.

DETAILED DESCRIPTION

Figure 1B:
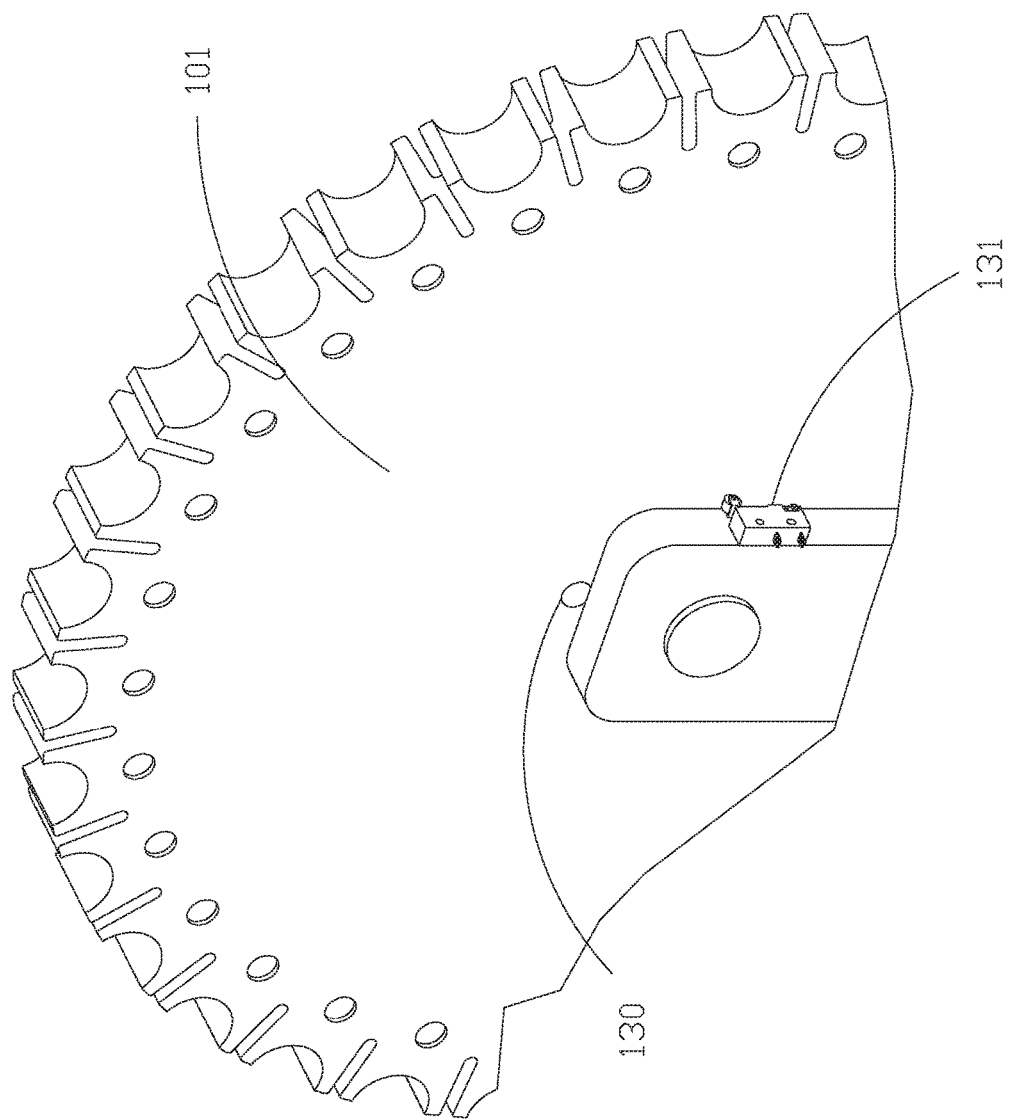
FIG. 1B is a partial perspective view of the same embodiment depicted in FIG. 1A with a view of a rear face of a wheel assembly.

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein. Like numbers refer to like elements throughout.

FIG. 1A is a perspective view of one embodiment of an automatic re-loading air-sampling and pneumatic transport system constructed in accordance with the teachings of the present invention with a view of a front face of a wheel assembly. In FIG. 1A, an embodiment of automatic re-loading air-sampling and pneumatic transport system 100 comprises a wheel assembly 101 and contains a plurality of chambers 103 comprising transverse cylindrical spaces with differently sized openings on opposite faces of the wheel assembly. For example, wheel assembly 101 may comprise thirty-two chambers 103, each having a 0.48" diameter, each chamber arranged 6.366" from the center of the wheel assembly, and each chamber spaced 1.2487" across an arc length measured from the center of each chamber. Other configurations of chambers 103 are also possible. For example, there may be a different number of chambers 103. They may be positioned at other distances from the center of the wheel assembly, and the wheel assembly 101 itself may be other sizes as well. The chambers 103 may be spaced at other arc length distances from each other. And they may have other diameters to accommodate other sizes and shapes of air-sampling cartridges 125 (or spherical air-sampling cartridges 141, see FIG. 1D). For example, chambers 103 may have a diameter (including spherical diameter) of 0.48 inches, 7/16 inches or ¼ inches. Wheel assembly 101 may be composed of Teflon-like Delrin® or any other suitable material known in the art. The chambers 103 may be arranged in a radial pattern equidistant from the center of the wheel assembly 101.

The wheel assembly 101 may have teeth 104 along its circumference for interaction with a rotating mechanism. In an embodiment, the depicted teeth 104 may be configured to interact with a specially designed cam 202 of a Geneva drive (see FIG. 2) to rotate the wheel assembly 101 between sampling and transport operations and stop the wheel assembly 101 during sampling and transport operations. The wheel assembly 101 can rotate on an axle 106 and may be held in place by a caliper assembly formed by a front wheel mount 107 and a rear wheel mount 108 attached to a support base 109. A vacuum line 110 from the vacuum pump 111 can be connected to a rear seal assembly 120 and configured to be aligned with an inlet tube 112 connected to a front seal assembly 121. A compressor line 115 from the compressor 116 may also be connected to the rear seal assembly 120 and configured to be aligned with an outlet tube 117 that is also connected to the front seal assembly 121.

In an embodiment of the invention, air-sampling cartridge 125 can be a rigid hollow cylinder with a media pad 126 on at least one end. Media pad 126 can comprise any of a variety of sampling media, including fibrous, membranous, and/or perforated media, as well as an adsorbent and/or gel-based media, depending on a variety of factors, including the intended aerosol to be analyzed. Other embodiments of the invention can use solid air-sampling cartridges 125 comprising a matrix of media including fiber, such as cellulose, without a separate media pad 126. In still other embodiments of the invention, air-sampling cartridge 125 can be a rigid hollow cylinder that is filled with sampling media, including fibrous, membranous, and/or perforated solid media, as well as adsorbents and/or gel-based media.

Some embodiments of the invention can attach an end-cap to the vacuum side of air-sampling cartridge 125. An end-cap can also be optionally attached to the vacuum side of media pad 126 (or the vacuum side of air-sampling cartridge 125 if media pad 126 is not used). An end-cap could be made of material such as Mylar film and could optionally include cut flaps that open during the sampling operation to allow airflow through the sampling media and then close during the transport operation to provide resistance against pneumatic pressure supplied by the compressor 116.

In other embodiments of the invention, air-sampling cartridge 125 may comprise a spherical air-sampling cartridge 141, as illustrated in FIG. 1D. Spherical air-sampling cartridge 141 may comprise sampling media such as fibrous, membranous, and/or perforated solid media, as well as adsorbents and/or gel-based media. As an example of a perforated solid media, spherical air-sampling cartridge 141 may comprise a porous (for example, 30-200 micron-sized pores) sphere made of polyethylene, polypropylene, or any similar polyolefin compound known in the art. One benefit of using a perforated solid media versus a fibrous media can include a lower probability of a stray fiber getting caught or pulled into the caliper assembly (formed by front wheel mount 107 and rear wheel mount 108) of an embodiment during rotation of wheel assembly 101. Spherical air-sampling cartridge 141 may have a diameter of approximately 7/16 inch, approximately ¼ inch, or any other suitable diameter that allows it to fit inside chamber 103 and travel through outlet tube 117 during a transport operation.

FIG. 1B is a partial perspective view of the same embodiment depicted in FIG. 1A with a view of a rear face of a wheel assembly. In FIG. 1B, the rear side of the wheel assembly 101 has at least one special cartridge marker 130 that comprises a partially drilled hole sensed by a special cartridge detector 131. The special cartridge detector 131 is in communication with a controller 611 (see FIG. 6B) that can indirectly rotate the wheel assembly 101 to a position where special cartridge marker 130 is sensed by special cartridge detector 131. When wheel assembly 101 is in this position, a specific chamber 103 associated with the special cartridge marker 130 is aligned at the sampling position. Using this technique of placing wheel assembly 101 in a known configuration, an operator can load air-sampling cartridges 125 (or spherical air-sampling cartridges 141) into chambers 103 associated with the special cartridge markers 130. Then, controllers within embodiments of the invention can be programmed to rotate wheel assembly 101 into a position where a specific chamber 103 associated with a special cartridge marker 130 is aligned with the sampling position. This operation can be performed by pre-programmed instructions within a controller or on demand via remote communication.

Figure 1C:
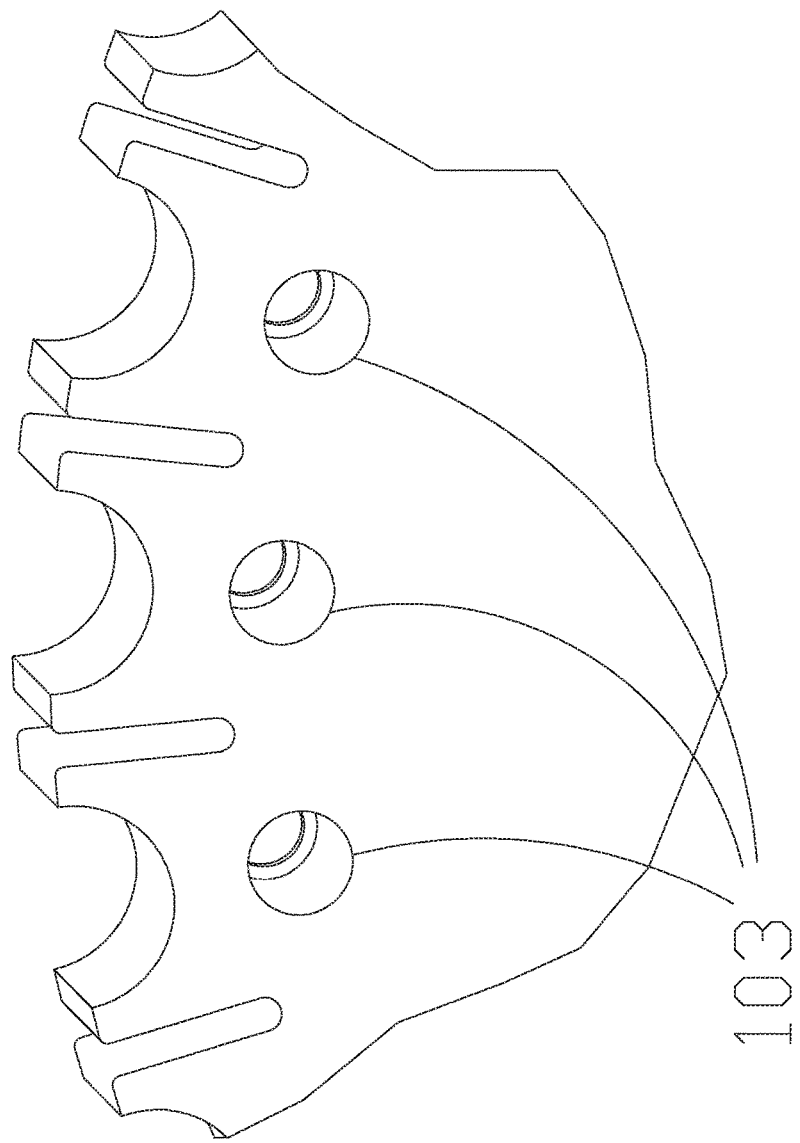
FIG. 1C is a partial perspective view of the same embodiment depicted in FIG. 1A with a view of the front face of the wheel assembly and the interior of some of its chambers.

FIG. 1C is a partial perspective view of the same embodiment depicted in FIG. 1A with a view of the front face of the wheel assembly 101 and the interior of some of the chambers 103. In FIG. 1C, the openings of the chambers 103 on the front face of the wheel assembly 101 have a diameter that is equal to or greater than the diameter of the air-sampling cartridges 125 (or spherical air-sampling cartridges 141). The openings of the chambers 103 on the rear face of the wheel assembly 101 have a diameter less than the diameter of the air-sampling cartridges 125 (or spherical air-sampling cartridges 141). The differently sized openings allow an air-sampling cartridge 125 (or spherical air-sampling cartridge 141) to be loaded through the larger opening on the front side of the wheel assembly 101 and remain retained in the wheel assembly 101 while air is drawn by the vacuum pump 111 through the smaller opening on the rear face of the wheel assembly 101 during sampling operation.

FIG. 1D is a partial perspective view of the same embodiment depicted in FIG. 1A with a view of the front face of the wheel assembly 101 and the interior of some of the chambers 103, illustrating a different embodiment that uses a spherical air-sampling cartridge (or filter) 141. In FIG. 1D, the openings of the chambers 103 on the front face of the wheel assembly 101 will preferably have a diameter that is equal to or slightly greater than the diameter of spherical air-sampling cartridges 141. Alternatively, the diameter of the spherical air-sampling cartridges 141 will preferably have a diameter that is equal to or slightly smaller than the diameter of the openings of the chambers 103. The openings of the chambers 103 on the rear face of the wheel assembly 101 will preferably have a diameter less than the diameter of the spherical air-sampling cartridges 141. The differently sized openings in a chamber 103 will allow a spherical air-sampling cartridge 141 to be loaded through the larger opening of chamber 103 on the front side of the wheel assembly 101 and remain retained in a chamber 103 while air is drawn by the vacuum pump 111 through the smaller opening of chamber 103 on the rear face of the wheel assembly 101 during the sampling operation. To retain a spherical air-sampling cartridge 141 in place within chamber 103, a groove 147 may cut in a front portion of chamber 103 to allow an O-ring gasket 145 to be seated there. The O-ring gasket 145 may protrude slightly into the interior of chamber 103 to hold the spherical air-sampling cartridge 141 in place during a sampling operation and still allow the spherical air-sampling cartridge 141 to be pushed out of chamber 103 by air pressure during the transport operation. Another O-ring gasket 143 (preferably a square-shaped O-ring gasket) can be pressed into the back end of chamber 103 where it can seat against the shoulder of the rear opening of chamber 103 on the rear face of wheel assembly 101. During air sampling, the spherical air-sampling cartridge 141 can be sucked up against O-ring gasket 143 to provide a tight seal.

Figure 2:
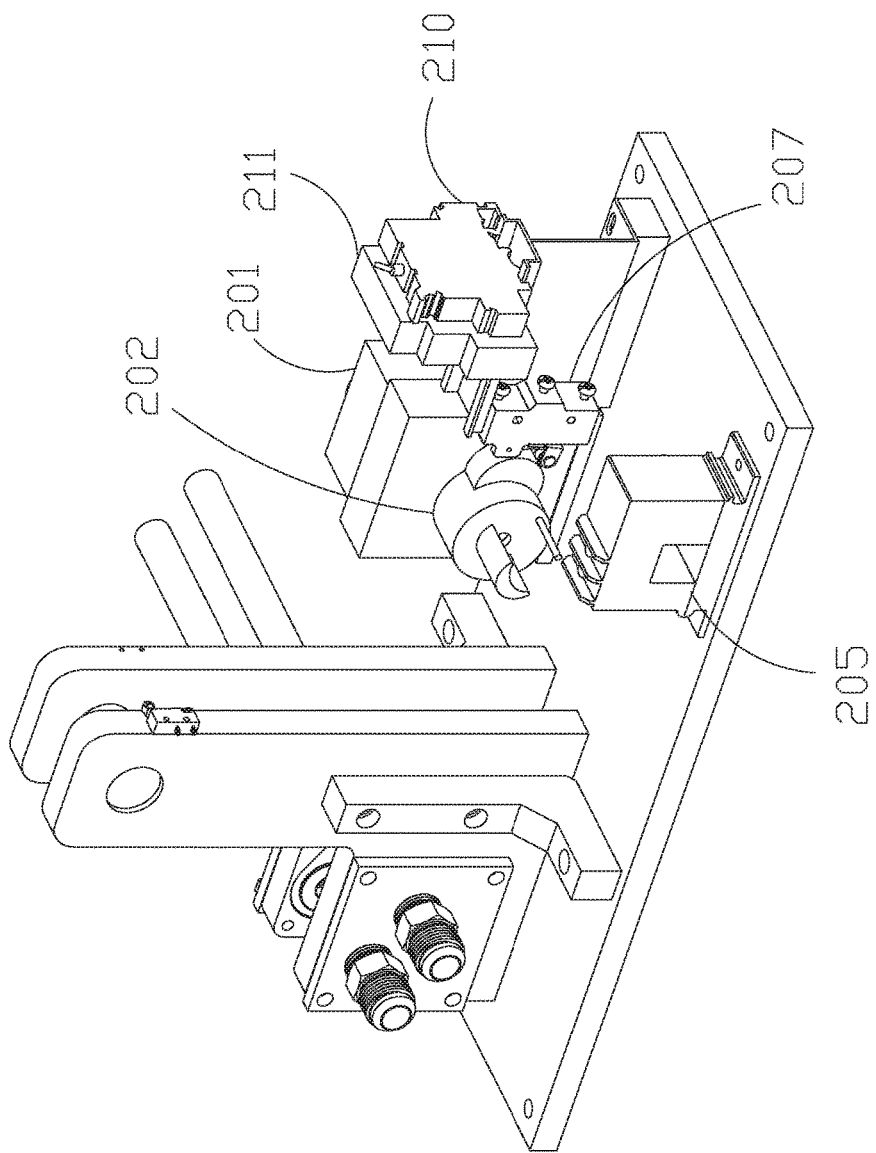
FIG. 2 is a partial perspective view of the embodiment depicted in FIG. 1A from the opposite side and with the wheel assembly removed.

FIG. 2 is a partial perspective view of the embodiment depicted in FIG. 1A from the opposite side and with the wheel assembly removed. In FIG. 2, the Geneva drive motor 201, or other rotation mechanism, rotates a cam 202 that interacts with the wheel assembly teeth 104 in such a way that each turn of the cam 202 rotates the wheel assembly 101 to advance each chamber 103 by one position. At each stop of the cam 202, one chamber 103 is in alignment with an inlet tube 112 and vacuum line 110 at a sampling position and a second chamber 103 is aligned with an outlet tube 117 and a compressor line 115 at a transport position. In this embodiment, when the Geneva drive motor 201 rotates the wheel assembly 101, all chambers 103 are advanced one position such that a chamber 103 retaining an unused air-sampling cartridge 125 (or spherical air-sampling cartridge 141) is advanced to the sampling position, the chamber retaining a now used air-sampling cartridge 125 (or spherical air-sampling cartridge 141) in the sampling position is advanced to the transport position, and the now empty chamber 103 in the transport position is advanced beyond the transport position.

A rocker switch 207 can cut power to the on/off switch 211 when triggered by the cam 202 and thereby stop rotation of the cam 201 and consequently hold the wheel assembly 101 in position. A current sensor 205 in communication with a controller can detect which electrical circuits connected to the Geneva drive motor 201 are energized in order for the controller to reactivate the Geneva drive motor 201 through the on/off switch 211. A manual switch 210 can allow an operator to manually trigger the Geneva drive motor 201 for loading air-sampling cartridges 125 (or spherical air-sampling cartridges 141) or for performing maintenance, if necessary.

Figure 3:
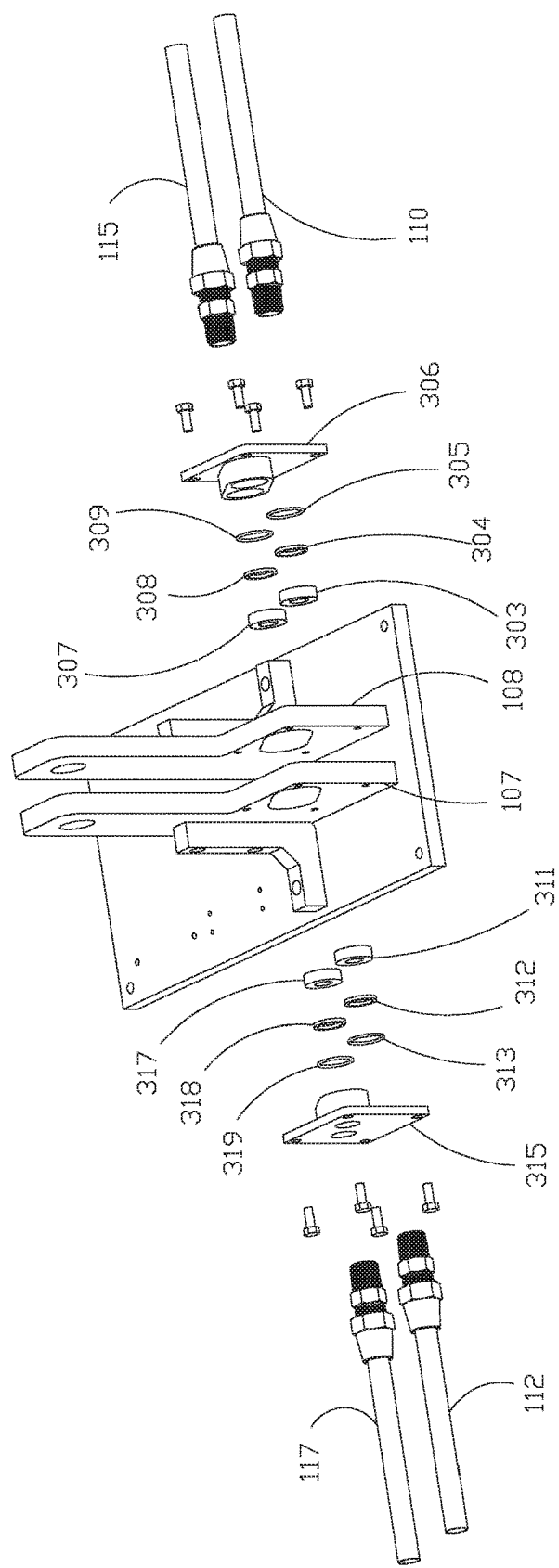
FIG. 3 is a partial perspective view of the embodiment illustrated in FIG. 1A and FIG. 2 showing an exploded view of the components that comprise the front seal assembly and rear seal assembly.

FIG. 3 is a partial perspective view of the embodiment illustrated in FIG. 1A and FIG. 2 showing an exploded view of the components that comprise the front seal assembly and rear seal assembly. In FIG. 3, the rear seal assembly 120 forms a substantially airtight seal between the vacuum line 110 and the rear face of the wheel assembly 101, while allowing free rotation of the wheel assembly 101, by biasing a double-lipped cup 303 with a wave spring washer 304 positioned between the double-lipped cup 303 and an O-ring 305 adjacent to a rear backing plate 306. The rear seal assembly 120 also forms a substantially airtight seal between the compressor line 115 and the rear face of the wheel assembly 101, while allowing free rotation of the wheel assembly 101, by biasing a double-lipped cup 307 with a wave spring washer 308 positioned between the double-lipped cup 307 and an O-ring 309 adjacent to the rear backing plate 306.

The front seal assembly 121 forms a substantially airtight seal between the inlet tube 112 and the front face of the wheel assembly 101, while allowing free rotation of the wheel assembly 101, by biasing a double-lipped cup 311 with a wave spring washer 312 positioned between the double-lipped cup 311 and an O-ring 313 adjacent to a front backing plate 315. The front seal assembly 121 also forms a substantially airtight seal between the outlet tube 117 and the front face of the wheel assembly 101, while allowing free rotation of the wheel assembly 101, by biasing a double-lipped cup 317 with a wave spring washer 318 positioned between the double-lipped cup 317 and an O-ring 319 adjacent to the front backing plate 315.

The rear backing plate 306 has a projection to retain the double-lipped cups 303, 307, wave spring washers 304, 308, and O-rings 305, 309. The front backing plate 315 has a projection to retain the double-lipped cups 311, 317, wave spring washers 312, 318, and O-rings 313, 319.

The rear wheel mount 108 has a cutaway to allow the projection of the rear backing plate 306 to pass through and approach the rear face of the wheel assembly 101. The front wheel mount 107 has a cutaway to allow the projection of the front backing plate 315 to pass through and approach the front face of the wheel assembly 101.

Figure 4:
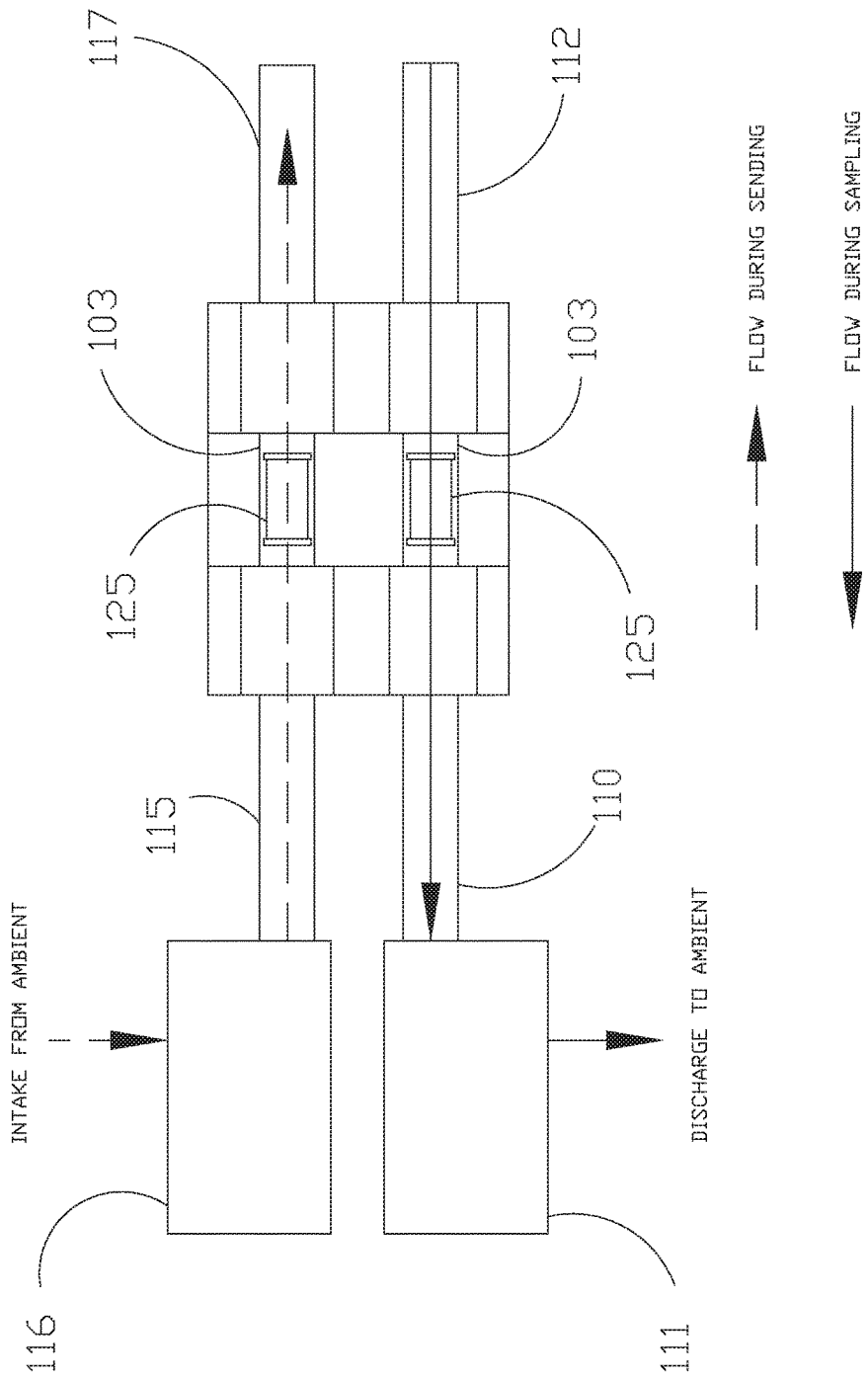
FIG. 4 is a schematic representation of the airflow pathways through an embodiment of the invention utilizing one compressor and one vacuum pump for separate sampling and transport operations.

FIG. 4 is a schematic representation of the airflow pathways through an embodiment of the invention utilizing one compressor and one vacuum pump for separate sampling and transport operations. In FIG. 4, during a sampling operation, ambient air is pulled in from the inlet tube 112, through an air-sampling cartridge 125 (or spherical air-sampling cartridge 141) retained in a chamber 103 at the sampling position, then through a vacuum line 110 to the vacuum pump 111, where the air is then discharged to the ambient environment. During, transport operation, ambient air is pulled in at the compressor 116, which then creates pneumatic pressure in the compressor line 115 and pushes an air-sampling cartridge 125 (or spherical air-sampling cartridge 141) retained in a chamber 103 at the transport position out through the outlet tube 117.

Figure 5:
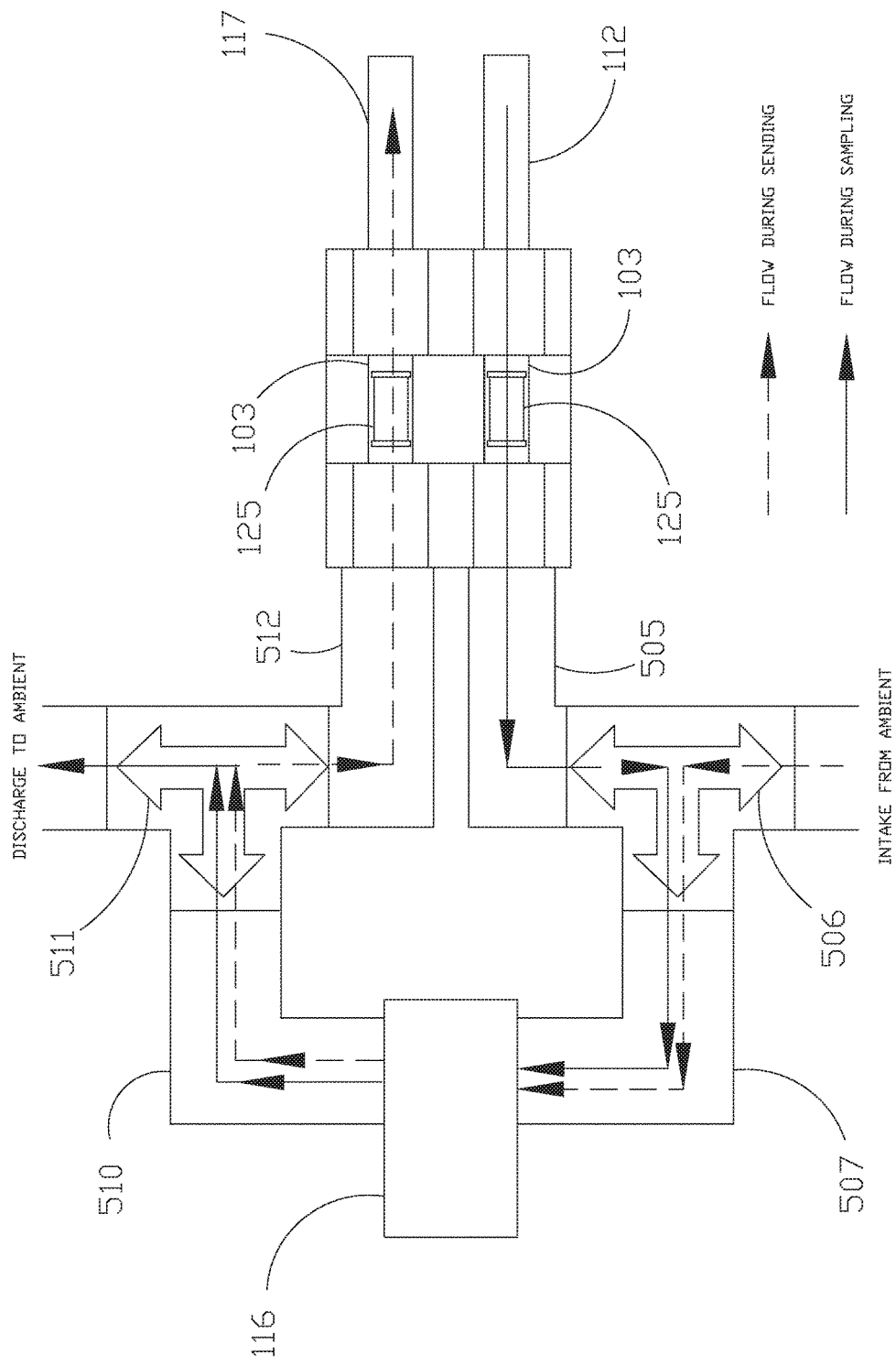
FIG. 5 is a schematic representation of the airflow pathways through an embodiment of the invention utilizing a single compressor and two three-way valves for both sampling operation and transport operation.

FIG. 5 is a schematic representation of the airflow pathways through an embodiment of the invention utilizing a single compressor and two three-way valves for both sampling operation and transport operation. In FIG. 5, during sampling operation, ambient air is pulled in from the inlet tube 112, through an air-sampling cartridge 125 (or spherical air-sampling cartridge 141) retained in a chamber 103 at the sampling position, through a first vacuum line 505 connected to a first three-way valve 506 set to direct air to a second vacuum line 507 connected to a compressor 116, where it is then discharged through a first compressor line 510 connected to a second three-way valve 511 set to discharge air into the ambient environment. During transport operation, the three-way valves are switched to direct air in following way: ambient air is pulled in from the first three-way valve 506 set to receive air from the ambient environment, then though the second vacuum line 507 to the compressor 116, which creates pneumatic pressure in the first compressor line 510 connected to the second three-way valve 511 set to direct air through a second compressor line 512 and push an air-sampling cartridge 125 (or spherical air-sampling cartridge 141) retained in a chamber 103 at the transport position out through the outlet tube 117 to a remote destination.

As mentioned above in the Summary, embodiments of the invention can incorporate radiological, chemical, and/or biological detectors to analyze samples within air-sampling cartridge 125 (or spherical air-sampling cartridge 141) before it is transported to a remote destination. Before transport, an air-sampling cartridge 125 (or spherical air-sampling cartridge 141) that has been retained in a chamber 103 during a sampling operation can be advanced from the sampling position and aligned with a detector at an analysis position where an air sample obtained at the sampling position can be analyzed while air-sampling cartridge 125 (or spherical air-sampling cartridge 141) is still loaded in chamber 103. Then, after analysis, the chamber 103 containing air-sampling cartridge 125 (or spherical air-sampling cartridge 141) can be advanced to the transport position, and the air-sampling cartridge 125 (or spherical air-sampling cartridge 141) containing the analyzed air sample can be transported out of its chamber 103 through the outlet tube 117, either to a remote destination or to a nearby collection container. Alternatively, instead of analyzing an air-sampling cartridge 125 (or spherical air-sampling cartridge 141) while it is loaded in chamber 103, air-sampling cartridge 125 (or spherical air-sampling cartridge 141) may be transported out of chamber 103 through the outlet tube 117 to a nearby location (including a location within the automatic re-loading air-sampling and pneumatic transport system 100), or to a remote destination, for analysis.

Figure 6B:
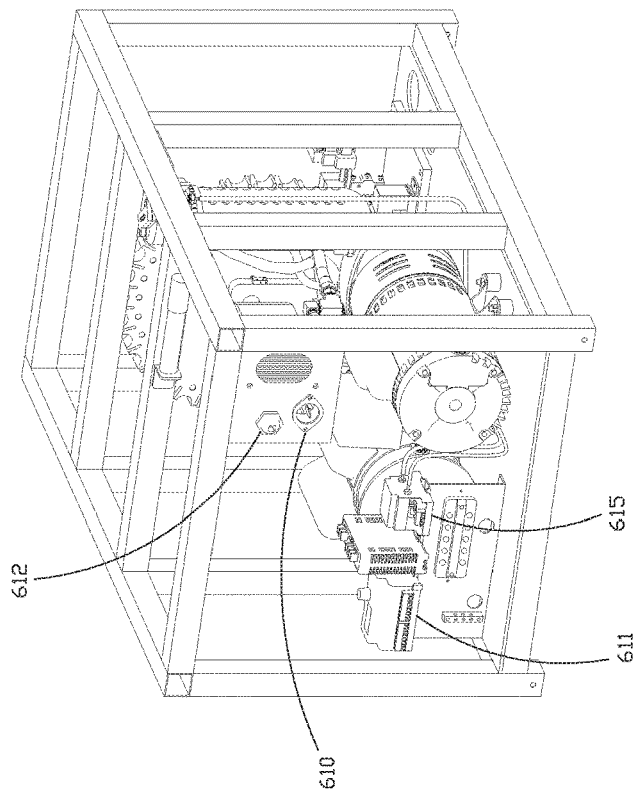
FIG. 6B is another partial perspective view of the same embodiment depicted in FIG. 6A with a view from the opposite side.
Figure 6A:
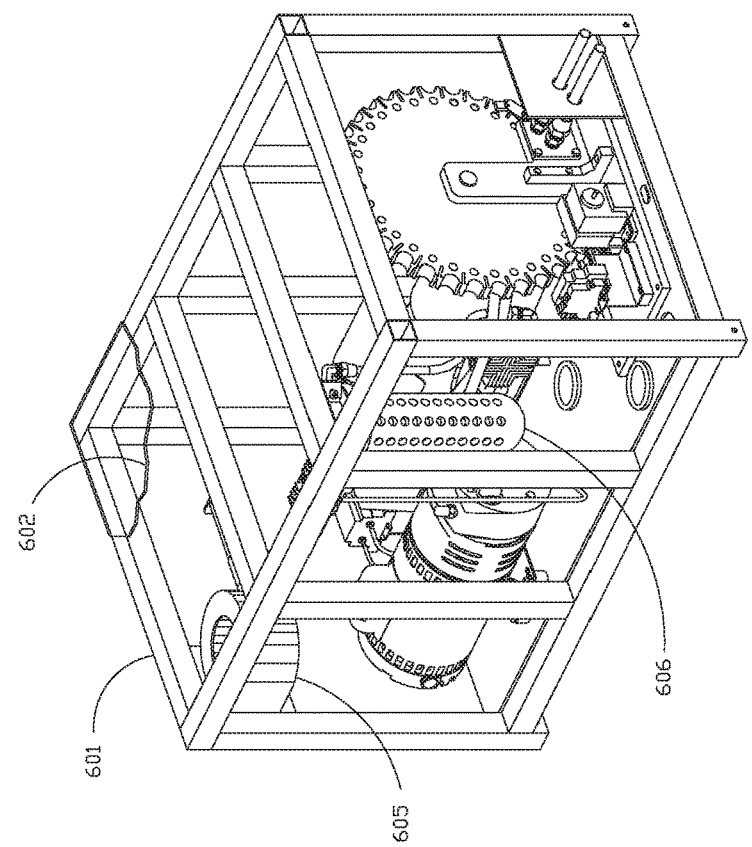
FIG. 6A is a partial perspective view of an embodiment of the invention encased within a chassis.

FIG. 6A is a partial perspective view of an embodiment of the invention encased within a chassis. In FIG. 6A, an embodiment of the invention can be housed in a chassis 601 that can be overlaid with cover plates 602. An internal fan 605 can be attached to the interior of chassis 601 to exhaust hot air. A desiccant assembly 606 can be connected between the compressor 116 and compressor line 115 to help prevent moisture accumulation in the outlet tube 117 and compressor line 115.

FIG. 6B is another partial perspective view of the same embodiment depicted in FIG. 6A with a view from the opposite side. In FIG. 6B, a power receptacle 610 can be attached to the chassis 601, which can distribute electricity from an external 110-220V power source to the vacuum pump 111, compressor 116, and controller 611 with associated communications board. A pressure transducer 615 can be connected to the compressor line 115 to measure the air pressure in the compressor line 115 and connected components, such as the aligned chamber 103 at the transport position and the outlet tube 117, and also connected to the vacuum line 110 to measure the air pressure in the vacuum line 110 and connected components, such as the aligned chamber 103 at the sampling position and the inlet tube 112. An Ethernet jack 612 that is in communication with controller 611 allows wired remote operation of the system. Alternatively, an embodiment of the invention can be equipped with a wireless communication module or chip that is in communication controller 611 and allows wireless remote operation of the system.

Figure 8A:
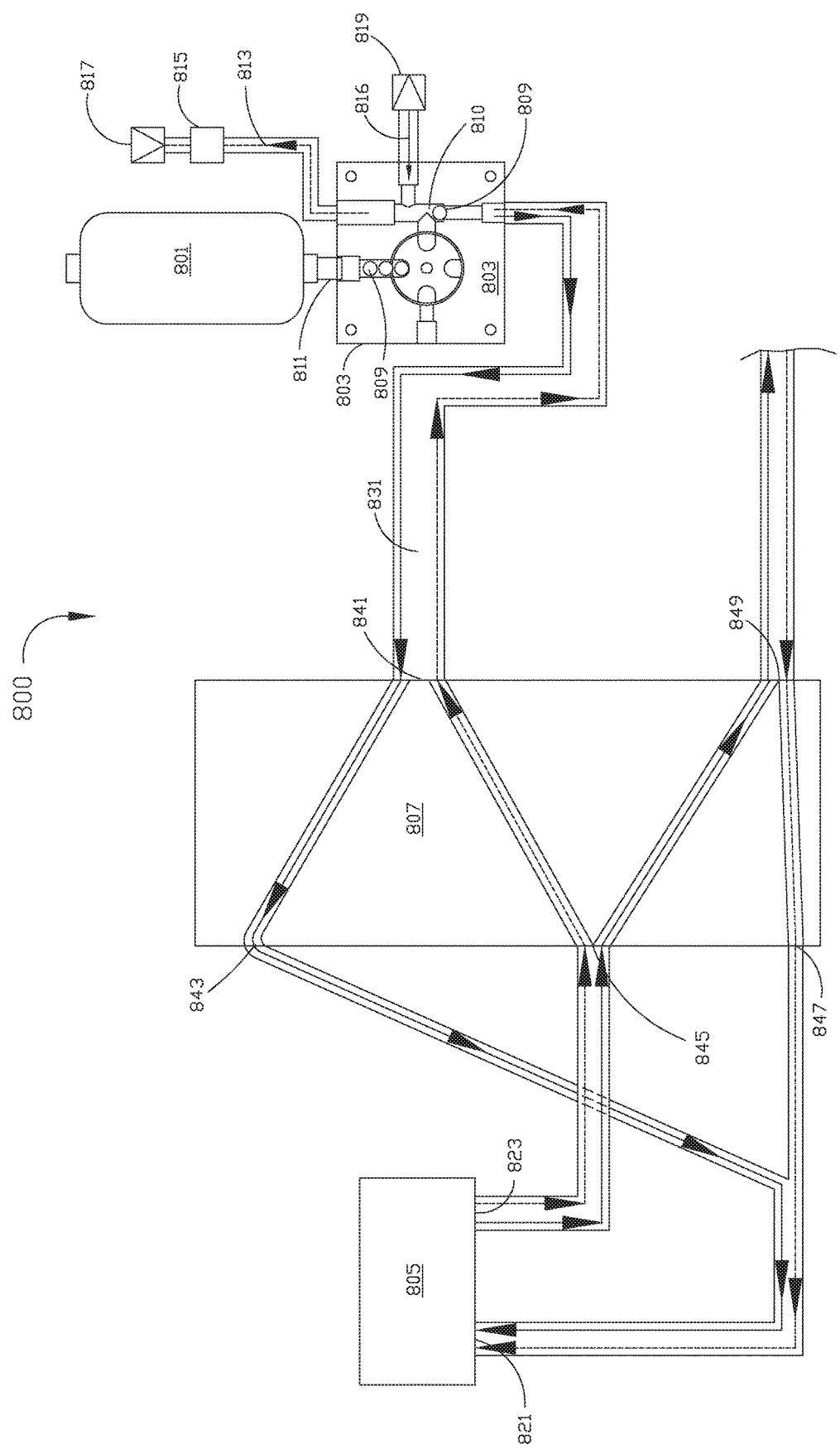
FIG. 8A is a schematic representation of an embodiment of the invention utilizing one compressor for both the sampling operation and the transport operation, a storage magazine for storing and supplying a plurality of spherical air-sampling filters (also called "ball filters"), and an integrated air-sampling manifold to facilitate both the sampling operation at the sampling position and the transport operation at the transport position.

FIG. 8A is a schematic representation of an embodiment of the invention that utilizes one compressor for both the sampling operation and the transport operation, utilizes a storage magazine or ball hopper (these terms are used interchangeably) for storing and supplying a plurality of spherical air-sampling filters (also called "ball filters"), and utilizes an integrated air-sampling manifold to receive ball filters from the ball hopper and to facilitate the sampling operation at the sampling position and the transport operation at the transport position. In FIG. 8A, an embodiment of an automatic re-loading air-sampling and pneumatic transport system 800 comprises a ball hopper 801, an air-sampling manifold 803, an air compressor 805, and an air valve 807. The arrowed lines in FIG. 8A indicate the direction of airflow during the sampling operation and the transport operation. Solid lines with arrows indicate the direction and path of airflow during the sampling operation. Dotted lines with arrows indicate the direction and path of airflow during the transport operation.

Automatic re-loading air-sampling and pneumatic transport system 800 can sample aerosols by utilizing air compressor 805 to pull ambient air through one-way check valve 819 and inlet tube 816 into air-sampling manifold 803, where a ball filter 809 has been placed in a sampling-transport position 810 to collect and/or concentrate aerosols and/or vapors. After a sufficient amount of air has been drawn through ball filter 809, air compressor 805 can then be used to transport the used ball filter 809 away from the sampling-transport position 810, out of air-sampling manifold 803, through an output tube 813, and to a filter retrieval container 815, which can be located nearby or at a remote location. (In this configuration of automatic re-loading air-sampling and pneumatic transport system 800, the sampling position and the transport position occupy the same location 810.) At filter retrieval container 815, the aerosols and/or vapors collected by ball filter 809 during a sampling operation can be analyzed in place, or ball filter 809 can be withdrawn from retrieval container 815 and transported to a different location for analysis. Output tube 813 can be any appropriate length, from a few inches to several miles.

Air compressor 805 can operate to pull air through an inlet port 821 and eject the same air through an outlet port 823. In operation, air compressor 805 can create an air inlet pressure of approximately −10 PSIG at inlet port 821 and an air outlet pressure of approximately +30 PSIG at outlet port 823. Air compressor 805 may be configured to operate at other pressures as well, depending on a variety of factors known to one skilled in the art, including the power of the compressor, the diameter of ball filter 809, the diameter of any tubes or conduits through which ball filter 809 will travel, the length of such tubes or conduits, the smoothness of the inner surfaces of the tubes and conduits, and speed at which the ball filter 809 should travel through the tubes and conduits, and the rate at which aerosols are expected to be collected from the ambient air.

Air valve 807 can enable air compressor 805 to operate in one of two modes: vacuum mode for a sampling operation or compressor mode for a transport operation, by changing the direction of air flowing through its internal chambers. Air valve 807 may have five ports: (1) a main port 841, though which air can flow between air valve 807 and air-sampling manifold 803; (2) an ambient air output port 843, through which ambient air acquired during a sampling operation can be pulled under a vacuum through inlet port 821 of air compressor 805; (3) a compressed air inlet port 845 that receives compressed air from outlet port 823 of air compressor 805; (4) an ambient air output port 847, through which ambient air can be acquired during a transport operation; and (5) an ambient air intake/exhaust port 849, through which ambient air can be acquired during a transport operation and through which sampled air can be exhausted to the environment during a sampling operation.

In vacuum mode during a sampling operation, air valve 807 can be configured to permit air to flow: from the ambient environment through a one-way check valve 819 and inlet tube 816 into a sampling-transport position 810 in air-sampling manifold 803 where the ambient air can penetrate a ball filter 809 and aerosols can be concentrated therein; away from the sampling-transport position 810 and out of air-sampling manifold 803 through tube 831 into air valve 807 through main port 841; out of air valve 807 through ambient air output port 843 into air compressor 805 through its inlet port 821; out of air compressor 805 through its outlet port 823 into air valve 807 through compressed air inlet port 845; and finally out of air valve 807 through ambient air intake/exhaust port 849 and into the ambient environment. One-way check valve 819 may permit air to enter the system 800 but not to exit from that point. The one-way feature of check valve 819 prohibits air, possibly carrying a used ball filter 809, from exiting the system 800 during a transport operation. Ambient air intake/exhaust port 849 may be optionally configured with a high-efficiency particulate arresting ("HEPA") filter (not shown) to lower the probability that exhaust air could contaminate the ambient environment near check valve 819 and inlet tube 816.

In compressor mode during a transport operation, air valve 807 can be configured to permit air to flow: from the ambient environment through an optional HEPA filter (not shown) connected to ambient air intake/exhaust port 849 into air valve 807; out of air valve 807 through ambient air output port 847 into air compressor 805 through its inlet port 821; out of air compressor 805 through its outlet port 823 into air valve 807 through compressed air inlet port 845; and finally out of air valve 807 through main port 841 into tube 831 and into air-sampling manifold 803, where a used ball filter 809 can be pneumatically transported from its sampling-transport location 810 in air-sampling manifold 803 through output tube 813 to filter retrieval container 815. Compressed air can be released into the ambient environment during a transport operation through one-way check valve 817. One-way check valve 817 may be optionally configured with a HEPA filter (not shown) to lower the probability that air exhausted from check valve 817 during a transport operation could contaminate the ambient environment, including the environment near input check valve 819 and/or inlet tube 816.

As will be readily apparent to one of skill in the art, other kinds and configurations of air valves, including multi-way ball valves, may be used in place of air valve 807, to alternately switch air pathways between a sampling operation and a transport operation, so a single air compressor 805 will be able to operate in both an intake-vacuum-sampling mode and an output-compression-transport mode.

Figure 8B:
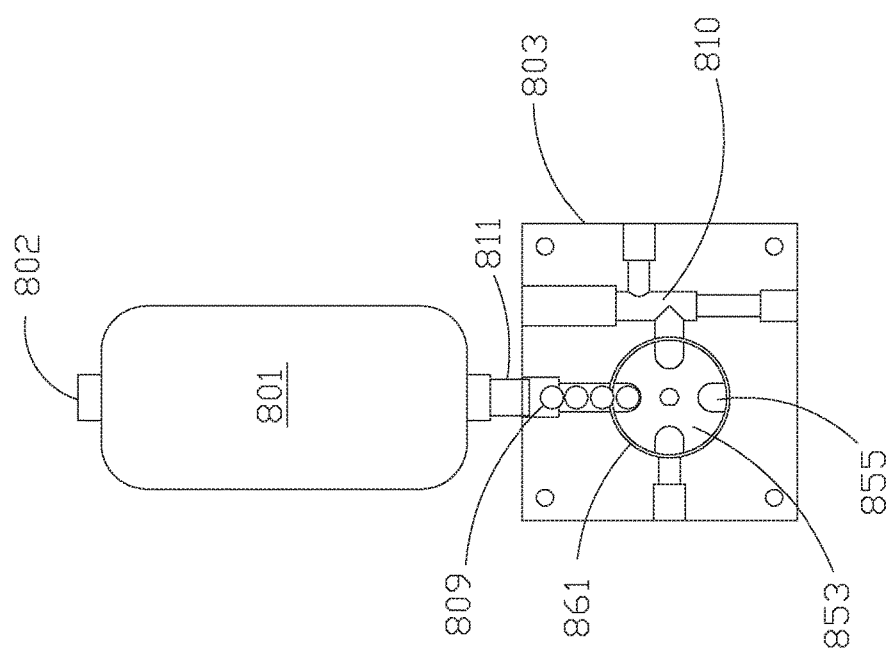
FIG. 8B is a more detailed schematic representation of the ball hopper and air-sampling manifold shown in FIG. 8A, in accordance with an embodiment of the invention.

FIG. 8B is a more detailed schematic representation of the ball hopper 801 and air-sampling manifold 803 originally shown in FIG. 8A, in accordance with embodiments of the invention. Ball hopper 801 is a container for supplying at least one and preferentially a plurality of ball filters 809 to an air-sampling manifold 803 through a conduit 811 that connects ball hopper 801 to air-sampling manifold 803 and through which a single ball filter 809 can pass, one at a time. Ball hopper 801 may be positioned substantially above air-sampling manifold 803 so that ball filters 809 can fall, one at a time, downward from ball hopper 801 through conduit 811 into air-sampling manifold 803 by action of gravity. Ball hopper 801 may be sized to hold any number of ball filters 809, and may have any one of a variety of shapes capable of holding a plurality of ball filters 809. As shown in FIGS. 8A and 8B, for example, ball hopper 801 may resemble a cylinder. Ball hopper 801 may have an opening 802 at the top for adding new (unused) ball filters 809.

FIG. 8B also illustrates an air-sampling manifold 803, which can receive a plurality of ball filters 809 through conduit 811. Conduit 811 may be preferably sized to permit only one ball filter 809 to pass through it at a time. As shown in FIG. 8B, several ball filters 809 may be staged in conduit 811 within air-sampling manifold 803.

A rotatable slotted drum 853 may be positioned within a retaining cylinder 861 within air-sampling manifold 803 and may be configured with a plurality of filter slots or filter pockets 855, each of which may sized and configured to receive one ball filter 809 when drum 853 is rotated within retaining cylinder 861 to align a filter pocket 855 with conduit 811, so a ball filter 809 can drop into pocket 855 by action of gravity. Once a ball filter 809 has dropped into a pocket 855, slotted drum 853 may then be rotated again to permit the ball filter 809 that dropped into pocket 855 to be delivered to a sampling-transport position 810 where ambient air can be drawn through the ball filter 809 to collect aerosols.

Figure 8C:
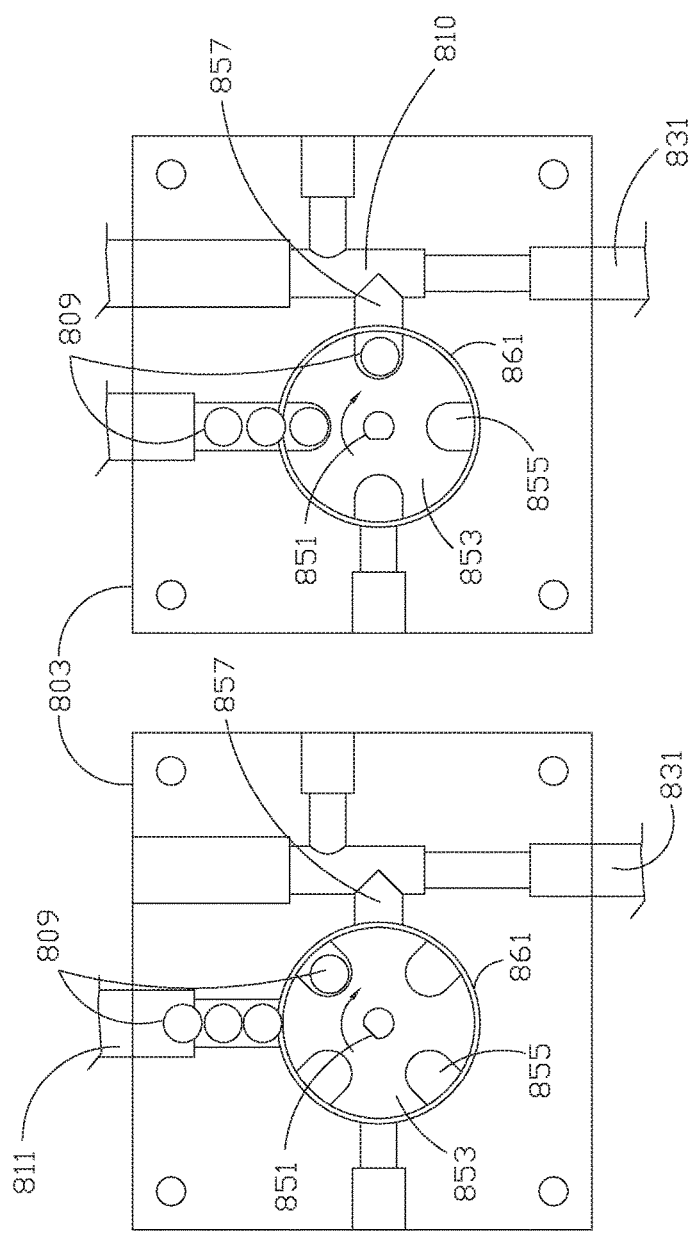
FIG. 8C is a detailed schematic representation of air-sampling manifold 803 originally shown in FIG. 8A, in accordance with an embodiment of the invention.

FIG. 8C is a detailed schematic representation of the air-sampling manifold 803 originally shown in FIG. 8A, in accordance with embodiments of the invention. In particular, FIG. 8C illustrates how slotted drum 853 can be rotated to move a ball filter 809 from conduit 811 into a sampling-transport position 810 where ambient air can be drawn over and through ball filter 809 to collect aerosols. On the left side of FIG. 8C, drum 853 is shown in a configuration where one of the plurality of pockets 855 has already received a ball filter 809 from conduit 811 and drum 853 has rotated approximately 45 degrees about keyed axis 851 within retaining cylinder 861 in the process of transporting ball filter 809 from a receiving position where pocket 855 is aligned with conduit 811 to a delivering position where pocket 855 is aligned with conduit 857. Drum 853 may be rotated by a stepper motor (not shown) that rotates drum 853 a predetermined number of degrees with each step. For example, a stepper motor can be configured to rotate drum 853 1.8 degrees per step, so that drum 853 will be rotated 180 degrees in 100 steps. Drum 853 can also be configured to include a sensor (not shown) to indicate when it is in a known position.

On the right side of FIG. 8C, drum 853 is shown in a configuration where it has rotated another 45 degrees about axis 851 within retaining cylinder 861 to a delivering position where the pocket 855 holding a ball filter 809 is aligned with conduit 857. In this configuration, ball filter 809 can be delivered from pocket 855 through conduit 857 to sampling-transport position 810 when a vacuum is applied to sampling-transport position 810 through tube 831.

When drum 853 is rotated within retaining cylinder 861 to move a pocket 855 toward conduit 857, the outer convex surface of drum 853 can act to block entrance of other ball filters 809 from entering the same pocket 855. As drum 853 rotates, other queued ball filters 809 stacked by gravity in conduit 811 can simply slide over the outer convex surface of drum 853 until the next pocket 855 rotates under conduit 811 and a ball filter 809 drops inside.

To improve air sample collection efficiency and maximize the probability that a ball filter 809 will be exposed only to air coming from the ambient environment and exposed to very little air from the area around air-sampling manifold 803 that might come from small spaces between drum 853 and retaining cylinder 861, once a ball filter 809 has been staged, either in conduit 857 or in sampling-transport position 810, drum 853 can be rotated so that no pocket 855 is in alignment with conduit 857, as shown, for example, on the left side of FIG. 8C.

As mentioned above, drum 853 can have a plurality of slots or filter pockets 855. FIGS. 8A-F illustrate embodiments of the present invention where drum 853 has exactly 4 pockets 855. As one skilled in the art will appreciate, a different number of pockets may be used. For example, drum 853 may have only one filter pocket 855, two filter pockets 855, three filter pockets 855, four filter pockets 855 (as shown in FIGS. 8A-F), or more than four filter pockets 855.

For example, in another embodiment, in addition to the filter pockets 855 that are used for normal operation, drum 853 may include one or more special-use pockets that are designated for use in certain special situations. The special-use pocket(s) can be one of the filter pockets 855. The special-use pocket(s) can be manually preloaded with a different kind of ball filter than is typically used for normal air sampling operations. For example, the special-use pocket(s) could be preloaded with a special ball filter for adsorbing, collecting, and/or concentrating certain kinds of vapors, once a ball filter 809 has been determined to have collected certain solid airborne particulates. The special-use pocket(s) can be configured with a unique gasket or gasket ring in order to retain the special ball filter in place when it rotates past conduit 857, but where the retaining power of the gasket or gasket ring can be overcome with sufficient vacuum so that a special ball filter can be pulled from its special-use pocket and loaded into sampling-transport position 810 when desired. Drum 853 may be configured with a position sensor to indicate the position of any of filter pockets 855, as well as the position of any special-use pockets. The position sensor can optionally be incorporated into the capability of a stepper motor that rotates and controls the position of drum 853.

Figure 8D:
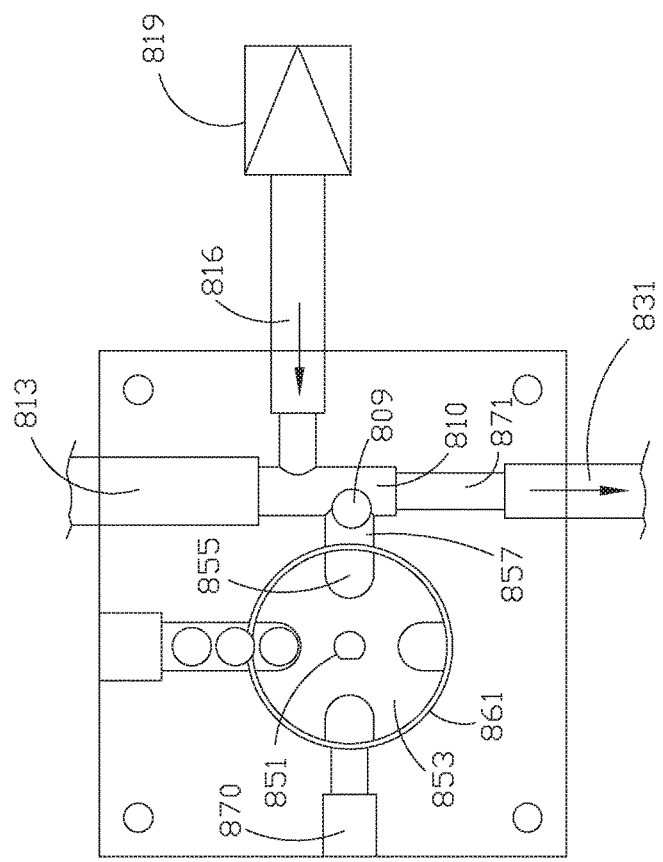
FIG. 8D is a detailed schematic representation of the air-sampling manifold 803 originally shown in FIG. 8A, in accordance with embodiments of the invention.

FIG. 8D is a detailed schematic representation of the air-sampling manifold 803 originally shown in FIG. 8A, in accordance with embodiments of the invention. In particular, FIG. 8D illustrates how a ball filter 809 that has been transported from conduit 811 to conduit 857 by drum 853 can be pulled from a pocket 855 into conduit 857. When a ball filter 809 is resting in a pocket 855 that is aligned with conduit 857, air valve 807 can be configured to operate in vacuum mode so that when compressor 805 is running, it will draw ambient air through one-way check valve 819 and inlet tube 816 into a sampling-transport position 810 and down tube 831. If, at that time, a ball filter 809 is resting in a pocket 855 that is aligned with conduit 857, it will be pulled away from pocket 855 and drawn through conduit 857 and toward sampling-transport position 810. To encourage movement of a ball filter 809 from a pocket 855 into conduit 857, air-sampling manifold 803 can be configured with an optional ambient air feed 870, through which ambient air may be drawn around drum 853 (for example, through the space between drum 853 and retaining cylinder 861) and into conduit 857, thereby "pushing" a ball filter 809 out of its pocket 855 and toward conduit 857.

Figure 8E:
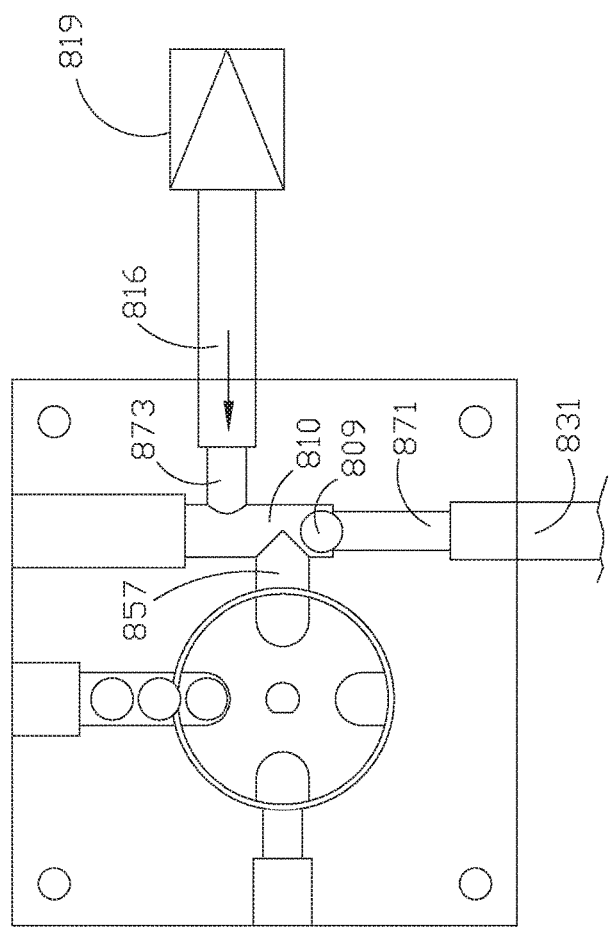
FIG. 8E is a detailed schematic representation of the air-sampling manifold 803 originally shown in FIG. 8A, in accordance with embodiments of the invention.

FIG. 8E is a detailed schematic representation of the air-sampling manifold 803 originally shown in FIG. 8A, in accordance with embodiments of the invention. In particular, FIG. 8E illustrates how a ball filter 809 that has been transported from conduit 811 to conduit 857 by drum 853 can be pulled from conduit 857 into a sampling-transport position 810 where ambient air can be drawn over and through ball filter 809 to collect aerosols. As compressor 805 continues to draw ambient air through one-way check valve 819 and inlet tube 816 into a sampling-transport position 810 and down tube 831, the ambient air will cause a ball filter residing in conduit 857 to be drawn further in the direction of the vacuum air flow, resulting in ball filter 809 being drawn into the sampling-transport position 810 shown in FIG. 8E. In this position, ball filter 809 will be blocked from moving into tube 831 by virtue of intervening conduit 871, which may have a smaller diameter than either conduit 857 or the sampling-transport position 810. In other words, conduit 871 may be preferably sized to have a diameter that does not permit entry or transportation of a ball filter 809.

Figure 8F:
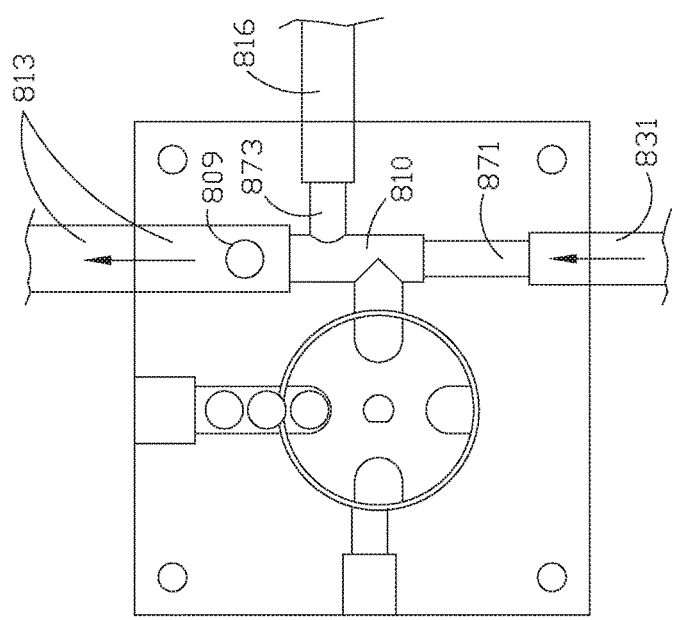
FIG. 8F is a detailed schematic representation of the air-sampling manifold 803 originally shown in FIG. 8A, which illustrates how a ball filter 809 can be transported away from the sampling-transport position 810 when compressor 805 is in compressor mode.

FIG. 8F is a detailed schematic representation of the air-sampling manifold 803 originally shown in FIG. 8A, which illustrates how a ball filter 809 can be transported away from the sampling-transport position 810 when compressor 805 is in compressor mode. In compressor mode during a transport operation, air valve 807 can be configured to permit air to flow: from the ambient environment through ambient air intake port 849 into air valve 807; out of air valve 807 through ambient air output port 843 into air compressor 805 through its inlet port 821; out of air compressor 805 through its outlet port 823 into air valve 807 through compressed air inlet port 845; and finally out of air valve 807 through main port 841 into tube 831, tube 871 of air-sampling manifold 803 and finally the sampling-transport position 810, from which a used ball filter 809 can be pneumatically transported from sampling-transport location 810 through output tube 813 to filter retrieval container 815 (shown in FIG. 8A), and the compressed exhaust air can exit from the automatic re-loading air-sampling and pneumatic transport system 800 through a one-way check valve 817 (shown in FIG. 8A), which also prohibits air from entering the system 800 during a sampling operation.

In the same way that conduit 871 may preferentially have a diameter that is smaller than a ball filter 809, conduit 873 may also preferentially have a diameter that is smaller than a ball filter 809. The purpose of the smaller diameters of these conduits is to prevent a ball filter 809 from accidentally moving into these conduits (and tubes, such as inlet tube 816) during a transport operation.

Some embodiments of the invention can utilize a combination of ball hopper 801 and air-sampling manifold 803 to load (or pre-load) chambers 103 of wheel assembly 101 with ball filters 809 (or spherical air-sampling cartridges 141). For example, air-sampling manifold 803 can be configured to align conduit 871, including sampling-transport position 810, with inlet tube 112. In this configuration, the combination of ball hopper 801 and air-sampling manifold 803 can stage a ball filter 809 (or spherical air-sampling cartridge 141) into sampling-transport position 810. Vacuum pump 111 can then pull ball filter 809 from sampling-transport position 810 into an empty chamber 103, where ball filter 809 can be held in place by O-ring gaskets 143 and 145 and used to sample air as described above. By subsequently rotating wheel assembly 101 so that each empty chamber 103 is aligned with inlet tube 112, wheel assembly 101 can be pre-loaded with ball filters or spherical air-sampling cartridges 141 supplied by the combination of ball hopper 801 and air-sampling manifold 803.

Figure 7:
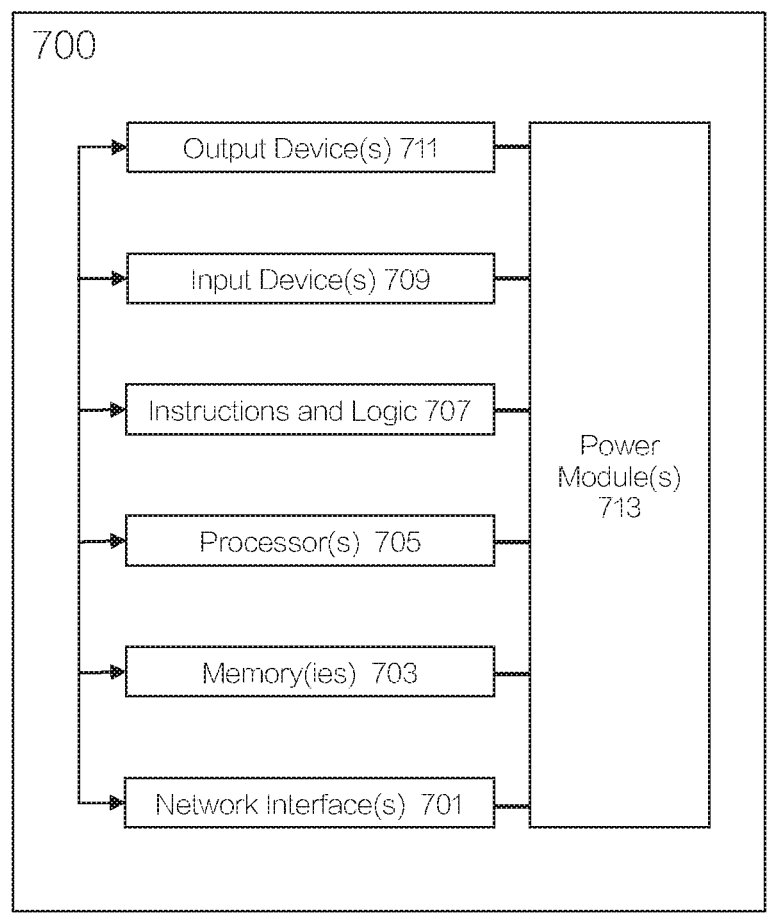
FIG. 7 is a block diagram of an exemplary embodiment of a computing device 700 that is configured to control the operation of various embodiments of the invention.

FIG. 7 is a block diagram of an exemplary embodiment of a computing device 700 that is configured to control the operation of various embodiments of the invention. In certain operative embodiments, computing device 700 is the controller 611 of FIG. 6B. Computing device 700 may comprise any device known in the art to be capable of processing data and/or information and also capable of being installed on or embedded within an embodiment of automatic re-loading air-sampling and pneumatic transport system 100 or air-sampling and pneumatic transport system 800. Accordingly, computing device 700 may comprise a general purpose and/or special purpose computer, including a microprocessor or microcontroller, a personal computer, workstation, server, minicomputer, microcomputer, computer terminal, laptop, tablet computer (such as an iPad), mobile terminal, smart phone (such as an iPhone, Android device, or BlackBerry) or the like. In general, any device on which resides a finite state machine capable of implementing at least a portion of a control operation, method, Application Programmer's Interface ("API"), communications interface, and/or user interface described herein may be used as a computing device. Computing device 700 may comprise any of numerous components, including one or more network interface(s) 701, one or more memory(ies) 703, one or more processor(s) 705, program instructions and logic 707, one or more input device(s) 709, one or more output device(s) 711, and one or more power module(s) 713.

Network interface(s) 701 may comprise any device, system, or subsystem or component that is capable of coupling an information device to a network and/or transmitting or receiving information. For example, a network interface can comprise a telephone, cellular phone, cellular modem, telephone data modem, fax modem, wireless transceiver, RF transceiver, Bluetooth transceiver, WiFi transceiver, wireless broadband transceiver (WiMAX), Ethernet circuit, cable modem, digital subscriber line interface, bridge, hub, router, or other similar capability.

Memory(ies) 703 can be any type of apparatus known in the art that is capable of storing analog or digital information such as instructions and/or data. Examples include a non-volatile or read only memory ("ROM"), volatile or random access memory ("RAM"), flash memory, various types of magnetic memory media, and the like. Memory(ies) 703 can be coupled to one or more processor(s) 705 and can store instructions and logic 707 adapted to be executed by one or more processor(s) 705, as according to any of the embodiments disclosed herein.

Processor(s) 705 may comprise one or more devices for executing machine-readable instructions that perform one or more predetermined tasks. Processor(s) 705 can comprise any one or a combination of hardware, firmware, and/or software. In general, processor(s) 705 can utilize mechanical, pneumatic, hydraulic, electrical, magnetic, optical, informational, chemical, and/or biological principles, signals, and/or inputs to perform tasks. In certain embodiments, processor(s) 705 can receive information from input device(s) 709. In certain embodiments, processor(s) 705 can act upon information, including received information, by manipulating, analyzing, modifying, converting, transmitting the information for use by an executable procedure and/or an information device, and/or routing the information to output device(s) 711. Processor(s) 705 can function as a central processing unit, local controller, remote controller, parallel controller, and/or distributed controller, etc. Processor(s) 705 can include a general-purpose device, such as a microcontroller and/or a microprocessor. In certain embodiments, processor(s) 705 can be a dedicated special purpose device, such as an Application Specific Integrated Circuit ("ASIC") or a Field Programmable Gate Array ("FPGA"). Processor(s) 705 can also be an integrated circuit that has been designed to implement in hardware and/or firmware at least a part of an embodiment disclosed herein. Processor(s) 705 can also include a hardware electronic logic circuit such as a discrete element circuit, and/or a programmable logic device such as a Programmable Logic Controller ("PLC") or the like.

Instructions and logic 707 may comprise directions adapted to cause a machine, such as computing device 700, to perform one or more particular activities, operations, or functions. The directions, which can sometimes form an entity called a "kernel", "operating system", "program", "application", "utility", "subroutine", "script", "macro", "file", "project", "module", "library", "class", "object", or "Application Programming Interface," etc., can be embodied as machine code, source code, object code, compiled code, assembled code, interpretable code, and/or executable code, etc., in hardware, firmware, and/or software. Instructions and logic 707 may reside in processor(s) 705, in memory(ies) 703, or in another specialized device(s) or component(s). Instructions and logic 707 may also be embedded in an external computer-readable storage medium or device, which when loaded into computing device 700 is able to carry out the different control instructions, steps, and methods described herein.

Input device(s) 709 may comprise any traditional input device known in the art, such as a button, dial, or switch, and may also include any sensory-oriented input device known in the art, such as an audio, visual, haptic, olfactory, and/or taste-oriented device, including, for example, a keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an input device can be attached or connected. Input device(s) 709 may also comprise any sensor known in the art that can measure physical/spatial parameters, including vibrations, acceleration, and direction of motion.

Output device(s) 711 may comprise any output device known in the art, such as, for example, a monitor, display, projector, overhead display, printer, switch, relay, solenoid, light-producing device, audio or sound-producing device, or vibrator, potentially including a port to which output device(s) 711 can be attached or connected.

Computing device 700 may be used, accessed, programmed, controlled, manipulated, or directed through a user interface. The user interface may comprise any means for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, auto-sizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

Power module(s) 713 may comprise one or more devices for providing electrical power to various the components of computing device 700. Power module(s) 713 may include one or more battery cells or other power supplies, any number of which can be electrically connected together. Some or all of the battery cells may be rechargeable. Power module(s) 713 may also include a power input to receive input power from a power source, and a power output to provide output power to another device, including another power module 713.

Embodiments of the invention can utilize computing device 700 to provide autonomous or manual-assisted control over various operations of automatic re-loading air-sampling and pneumatic transport system 100. Said operation can include, but is not limited to: receiving electronic communications and commands via Ethernet jack 612, controlling Geneva drive motor 201, activating and terminating operation of vacuum pump 111, activating and terminating operation of compressor 116, and three-way valves 506 and 511, as explained above.

Embodiments of the invention can also utilize computing device 700 to provide autonomous or manual-assisted control over various operations of air-sampling and pneumatic transport system 800. Said operation can include, but is not limited to: receiving electronic communications and commands via Ethernet jack 612 to control air valve 807, to control drum 853 (including a stepper motor for drum 853), and optionally to control operation of compressor 805, as explained above.

In addition to the illustrated embodiments, one of ordinary skill in the art will understand that an alternative embodiment of the invention can include a detection system such that air samples can be analyzed after sampling but prior to transport. With respect to automatic re-loading air-sampling and pneumatic transport system 100, such a detection system can analyze collected air samples while an air-sampling cartridge 125 (or spherical air-sampling cartridge 141) is still retained in a chamber 103 of the wheel assembly 101. With respect to air-sampling and pneumatic transport system 800, such a detection system can analyze air samples sent internally or externally while a ball filter 809 is still retained in filter retrieval container 815. Such alternative embodiments of the invention can include detectors to detect specific chemical compounds, biological components, and/or radiological emissions from an air sample.

The foregoing disclosure has been set forth merely to illustrate the invention and is not intended to be limiting. It will be appreciated that modifications, variations and additional embodiments are covered by the above teachings and within the purview of the appended claims without departing from the spirit and intended scope of the invention. Other logic may also be provided as part of the exemplary embodiments but are left out here so as not to obfuscate the present invention. Since modifications of the disclosed embodiments incorporating the spirit and substance of the invention may occur to persons skilled in the art, the invention should be construed to include everything within the scope of the appended claims and equivalents thereof.

The invention claimed is:

1. An apparatus for sampling air, comprising:
   (a) a hopper for holding a plurality of spherical air-sampling filters, said hopper having a top opening for receiving such filters, said hopper having a bottom opening for dispensing such filters, the bottom opening configured to permit only one such filter at a time to be dispensed from the hopper;
   (b) an air-sampling manifold coupled to the hopper's bottom opening via a filter supply conduit for transporting at least one of the filters at a time from the hopper to the manifold, said manifold comprising:
      (1) a rotatable drum retained in a circular enclosure within the manifold, where said circular enclosure is in communication with the filter supply conduit, where said circular enclosure is also in communication with a filter staging conduit, where said drum includes a filter chamber recessed within the circumferential surface of the drum, where the filter chamber is configured to receive one of the filters via the filter supply conduit when the drum is rotated to align the filter chamber with the filter supply conduit, and where the filter chamber is configured to supply the received filter to the filter staging conduit when the drum is rotated to align the filter chamber with the filter staging conduit;
      (2) a rotating mechanism configured to rotate the drum to align the filter chamber with the filter supply conduit, the rotating mechanism further configured to rotate the drum to align the filter chamber with the filter staging conduit; and
      (3) an air-sampling chamber in communication with the filter staging conduit, an ambient air input conduit, a filter output conduit, and an air compressor conduit;
   (c) an air compressor in communication with the air-sampling chamber via the air compressor conduit, where the air compressor is configured to pull ambient air from the ambient air inlet conduit and the air-sampling chamber in order to draw the filter retained in the filter staging conduit into the air-sampling chamber and then to continue pulling ambient air from the ambient air inlet conduit through the filter while the filter is retained in the air-sampling chamber, and where the air compressor is further configured to pneumatically push the filter from the air-sampling chamber through the filter output conduit into an outlet tube.

2. The apparatus of claim 1 where the rotating mechanism comprises a stepper motor.

3. The apparatus of claim 1, wherein each of said plurality of spherical air-sampling filters comprises fibrous, membranous, and/or perforated solid media for collecting airborne particulate matter.

4. The apparatus of claim 1, wherein each of said plurality of spherical air-sampling filters comprises adsorbent media for collecting vapors.

5. The apparatus of claim 1, wherein each of said plurality of spherical air-sampling filters comprises porous polyethylene.

6. The apparatus of claim 1, wherein each of said plurality of spherical air-sampling filters comprises porous polypropylene.

* * * * *